United States Patent
Harel et al.

(10) Patent No.: US 12,213,772 B2
(45) Date of Patent: Feb. 4, 2025

(54) SYSTEMS AND METHODS FOR REMOTELY TRACKING LIFE SIGNS WITH A MILLIMETER-WAVE RADAR

(71) Applicant: VAYYAR IMAGING LTD., Yehud (IL)

(72) Inventors: Tom Harel, Shefayim (IL); Yuval Lomnitz, Herzeliya (IL); Michael Orlovsky, Hod Hasharon (IL); Shay Moshe, Petach Tikva (IL); Naftali Chayat, Kfar Saba (IL); Alexei Khazan, Rosh Haayin (IL); Mark Popov, Ramat Gan (IL); Rohi Halimi, Shokeda (IL); Harel Golombek, Netanya (IL)

( * ) Notice: Subject to any disclaimer, the term of this patent is extended or adjusted under 35 U.S.C. 154(b) by 376 days.

(21) Appl. No.: 17/800,643

(22) PCT Filed: Feb. 18, 2021

(86) PCT No.: PCT/IB2021/051380
§ 371 (c)(1),
(2) Date: Aug. 18, 2022

(87) PCT Pub. No.: WO2021/165873
PCT Pub. Date: Aug. 26, 2021

(65) Prior Publication Data
US 2023/0337928 A1    Oct. 26, 2023

Related U.S. Application Data

(60) Provisional application No. 63/135,782, filed on Jan. 11, 2021, provisional application No. 63/069,050, (Continued)

(51) Int. Cl.
*A61B 5/05*    (2021.01)
*G01S 7/41*    (2006.01)
*G01S 13/534*    (2006.01)

(52) U.S. Cl.
CPC ............. *A61B 5/05* (2013.01); *G01S 7/415* (2013.01); *G01S 13/534* (2013.01)

(58) Field of Classification Search
CPC .......... A61B 5/05; G01S 7/415; G01S 13/534
(Continued)

(56) References Cited

U.S. PATENT DOCUMENTS 7,689,021 B2 *   3/2010  Shekhar ............... G06V 10/755
                                                  600/443
8,285,364 B2 *  10/2012  Barbagli .................. A61B 5/06
                                                  600/459
(Continued)

FOREIGN PATENT DOCUMENTS

WO    2008001092 A2    1/2008

OTHER PUBLICATIONS

Will et al., "Radar-Based Heart Sound Detection." Scientific Reports, Jul. 26, 2018, pp. 1-14 [online] https://www.nature.com/articles/s41598-018-29984-5.pdf.

*Primary Examiner* — Nuzhat Pervin
(74) *Attorney, Agent, or Firm* — AlphaPatent Associates Ltd.; Daniel J. Swirsky

(57) ABSTRACT

Systems and methods for monitoring life signs in a subject. A radar unit comprising generates raw data and a processor unit receives raw data and identifies oscillating signals in a series of arrays of complex values representing radiation reflected from each voxel of a target region during a given time segment. A phase value is determined for each voxel in each frame and a waveform representing phase changes over time for each voxel is generated. Voxels indicating an oscillating signal are selected and life sign parameters are extracted.

8 Claims, 22 Drawing Sheets

Related U.S. Application Data filed on Aug. 23, 2020, provisional application No. 63/030,943, filed on May 28, 2020, provisional application No. 63/021,373, filed on May 7, 2020, provisional application No. 62/977,902, filed on Feb. 18, 2020.

(58) Field of Classification Search
USPC ............................................. 600/407
See application file for complete search history.

(56) References Cited

U.S. PATENT DOCUMENTS

| | | | | |
|---|---|---|---|---|
| 9,568,594 | B2* | 2/2017 | Harash | G01S 13/89 |
| 9,576,468 | B2* | 2/2017 | Zack | H04B 1/7163 |
| 9,990,712 | B2* | 6/2018 | Gazit | A61B 6/5211 |
| 10,037,671 | B2* | 7/2018 | Zack | G08B 25/016 |
| 10,617,325 | B2* | 4/2020 | Chan | A61B 5/08 |
| 11,284,827 | B2* | 3/2022 | Telenkov | A61B 5/352 |
| 11,941,817 | B2* | 3/2024 | Richter | G06T 7/11 |
| 2010/0185102 | A1* | 7/2010 | Saar | A61N 5/1049 |
| | | | | 342/21 |
| 2010/0292568 | A1* | 11/2010 | Droitcour | G01S 13/88 |
| | | | | 600/425 |
| 2013/0116561 | A1* | 5/2013 | Rothberg | A61B 8/4477 |
| | | | | 600/459 |
| 2018/0192919 | A1* | 7/2018 | Nakayama | A61B 5/1116 |
| 2019/0209116 | A1* | 7/2019 | Sjöstrand | G16H 50/30 |
| 2019/0254544 | A1* | 8/2019 | Chayat | G01S 7/415 |
| 2021/0052176 | A1* | 2/2021 | Sarely | G01S 7/415 |
| 2021/0093203 | A1* | 4/2021 | Zhong | A61B 5/0507 |
| 2021/0245763 | A1* | 8/2021 | Gomez | G01S 7/2883 |

* cited by examiner

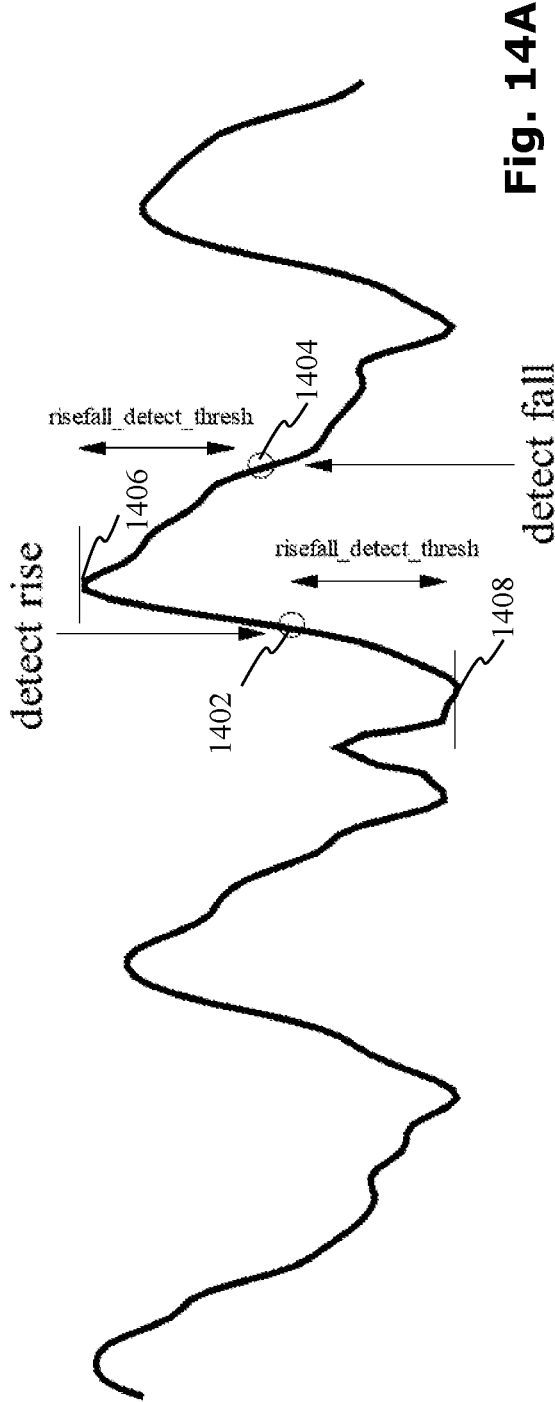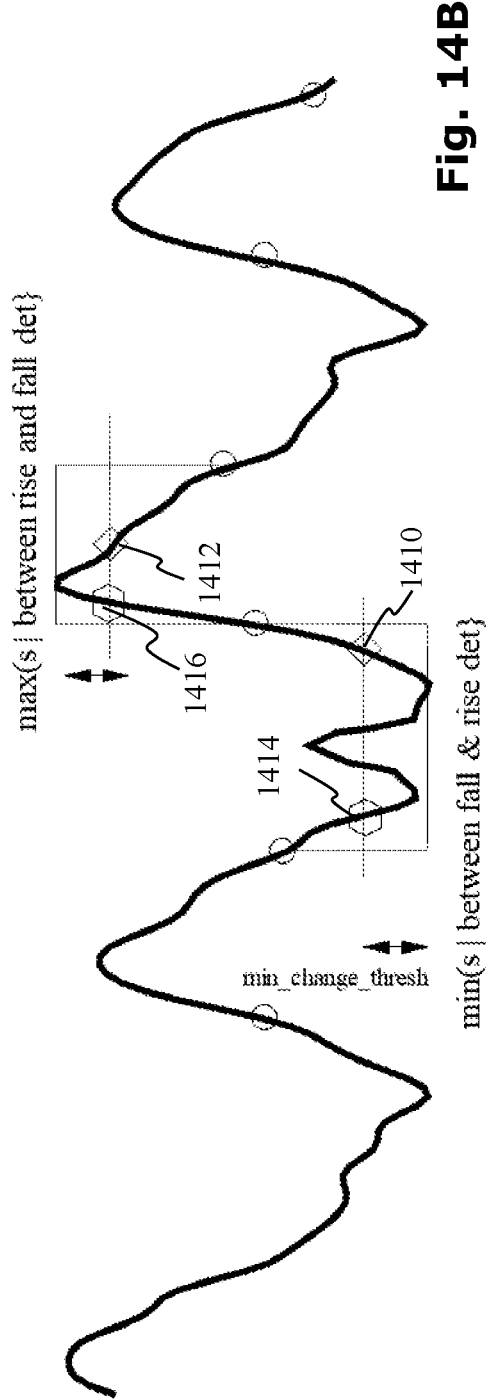
Fig. 14A
Fig. 14B

SYSTEMS AND METHODS FOR REMOTELY TRACKING LIFE SIGNS WITH A MILLIMETER-WAVE RADAR

CROSS-REFERENCE TO RELATED APPLICATIONS

This application is a U.S. National Phase Application under 35 U.S.C. 371 of International Application No. PCT/IB2021/051380, which has an international filing date of Dec. 23, 2020, which claims the benefit of priority from U.S. Provisional Patent Application No. 62/977,902 filed on Feb. 18, 2020, U.S. Provisional Patent Application No. 63/030,943 filed on May 28, 2020, U.S. Provisional Patent Application No. 63/021,373 filed on May 7, 2020, U.S. Provisional Patent Application No. 63/069,050, filed Aug. 23, 2020 and U.S. Provisional Patent Application No. 63/135,782, filed Jan. 11, 2021 the contents of which are incorporated by reference in their entirety.

FIELD OF THE DISCLOSURE

The disclosure herein relates to systems and methods for monitoring the life signs of individuals by using millimeter-wave radar. In particular the disclosure relates to systems and methods for tracking the displacement of body parts due to the breathing cycle and monitoring breathing characteristics, heart rate or pulse patterns.

BACKGROUND

A well-known method for detection of small displacement in narrowband radar systems exploits variation of the phase of the received signal over time. This method is often best carried out by first selecting voxels best suited for frequency determination.

Nevertheless, it is challenging to choose the best Voxels from which the breathing pattern is extracted, while being robust to other movements and noise. This disclosure deals with the selection of Voxels, extraction of waveform from the phase variation of the selected Voxels, and combining of the breathing waveform from multiple Voxels.

The need remains for efficient and reliable remote life signs monitoring. The invention described herein addresses the above-described needs.

SUMMARY OF THE EMBODIMENTS

According to one aspect of the presently disclosed subject matter, a method is hereby taught for monitoring life signs in a subject within a target region. The method may include providing a radar unit comprising at least one transmitter antenna connected to an oscillator and configured to transmit electromagnetic waves into the target region, and at least one receiver antenna configured to receive electromagnetic waves reflected by objects within the target region and operable to generate raw data. The method may further include providing a processor unit configured to receive raw data from the radar unit and operable to identify oscillating signals therein.

The radar may transmit and receive scanning radiation over the target region; the radar may generate a series of frames, each frame comprising an array of complex values representing radiation reflected from each voxel of the target region during a given time segment. Accordingly, the processor may collate a series of complex values for each voxel representing reflected radiation for the associated voxel in multiple frames. The method may further include for each voxel determining a center point in the complex plane; determining a phase value for each voxel in each frame; generating a smooth waveform representing phase changes over time for each voxel; selecting a subset of voxels indicative of an oscillating signal; and extracting life signs parameters from the oscillating signal.

Optionally, the step of selecting a subset of voxels indicative of an oscillating signal comprises selecting a subset of voxels indicative of a breathing pattern.

Additionally or alternatively, the step of selecting a subset of voxels indicative of an oscillating signal comprises: calculating an arc-fitting metric to the phase values associated with each voxel; and selecting voxels having an arc-fitting metric above a threshold value.

Again additionally or alternatively, the step of selecting a subset of voxels indicative of an oscillating signal comprises: calculating a time dependency function for the phase values associated with each voxel; and selecting voxels having periodic characteristics indicative of breathing. For example, the periodic characteristics indicative of breathing are selected from frequency; inhalation duration, exhalation duration, breath rate and combinations thereof.

In still other example of the method, the step of selecting a subset of voxels indicative of an oscillating signal comprises: generating a line segment model for the oscillating signal; extracting characteristic features from the line segment model; and executing a verification function to determine if the line segment model indicates a true-breathing signal.

Optionally, the step of generating a line segment model comprises: selecting bounding points for each significant sloped section in the oscillating signal wherein the bounding points of each significant sloped section comprise: a slope start point indicating a significant change from the previous extreme; and a slope end point which shares a y-coordinate with the subsequent slope start point of the next significant sloped section.

Accordingly, the step of generating a line segment model may further comprise constructing a trapezoid line segment model by constructing line segments between the bounding points of each significant sloped section, and constructing line segments between the end point of each significant sloped section and the start point of the next significant sloped section.

Additionally or alternatively, the step of selecting bounding points may comprise defining a detection threshold; sampling signal values in the oscillating signal until an extreme signal is detected; detecting the extreme signal point; sampling signal values in the oscillating signal after the extreme signal is detected; calculating the difference between each sampled signal and the extreme signal; and, if the difference is greater than the detection threshold, then setting a slope start point for a line segment following the extreme signal; and setting a slope end point for a line segment preceding the extreme signal. Accordingly, the step of setting a slope start point for a line segment following the extreme signal may comprise selecting the first signal following the extreme signal. Optionally, the step of setting a slope end point for a line segment preceding the extreme signal comprises selecting a signal sample before the extreme having a signal value equal to that of the slope start value.

In particular examples of the method, the step of selecting a subset of voxels indicative of a breathing pattern comprises: providing a breathing parameter determination module comprising a prefilter, a point generation module, a feature extraction module, a metric generation module and a breathing signal identification module; the prefilter providing a candidate signal to the point generation module; the point generation module generating a line segment model corresponding to the candidate signal; the feature extraction module receiving the line segment model and extracting characteristic features from the line segment model; the metric generation module processing the characteristic features to calculate characteristic metrics indicating probability that each feature is consistent with a breathing pattern; the breathing signal identification module receiving the characteristic metrics and determining a probability that the candidate signal represents a breathing signal.

Accordingly, the step of the metric generation module processing the characteristic features to calculate characteristic metrics may include: generating a log likelihood ratio (LLR) for each feature; assigning positing or negative signs to each LLR for each feature; and summing the LLR values.

Optionally, the step of extracting life signs parameters from the oscillating signal comprises determining heart rate rate parameters. Where required, this may include removing breathing related oscillation from the oscillating signal, possibly by obtaining a set of reference signal profiles having known heart rates; applying a line segment approximation to graph of phase values over time; applying a high pass filter to identify only oscillation above a threshold frequency value; applying a correlator to compare the filtered phase signal with each of the set of reference signal profiles; acquiring a characteristic reference correlation profile; selecting the peak correlation heart rate value; and, optionally, further applying validation rules such that only likely heart rates are selected.

Where appropriate, the step of providing the radar monitor comprises: providing a first radar transceiver device directed towards a common target region from a first angle, and providing a second radar transceiver device directed towards the common target region from a second angle, and the step of removing breathing related oscillations from the data comprises summing the phases signals received from the first radar transceiver to the phase signals received from the second radar transceivers such that radial movements are removed.

Accordingly, the step of removing breathing related oscillations from the oscillating signal may comprise obtaining a set of phase values associated with energy reflected from a selected voxel of the target region at a set of sequential timeframes; creating a delta file by subtracting from phase value at each timeframe, the phase value of the previous time frame; and subtracting the moving average of the phase values.

Additionally or alternatively the step of determining heart rate rate parameters may comprise: obtaining a heart rate signal; acquiring a characteristic reference correlation profile indicating degree of periodicity of the heart rate signal as a function of candidate heart rates; and selecting a heart rate value corresponding to peak periodicity correlation. Optionally, the step acquiring a characteristic reference correlation profile indicating degree of periodicity of the heart rate signal as a function of candidate heart rates comprises: sampling a section of the heart rate signal; for each of a set of candidate heart rates: segmenting the section of the heart rate signal into a number of segment-windows of equal duration corresponding to the period of a particular candidate heart rate; and correlating adjacent segment-windows to obtain a correlation index indicating a degree of periodicity corresponding to the candidate heart rate.

In various examples of the method, the step of determining a phase value for each voxel in each frame includes: the processor collating a series of complex values for each voxel representing reflected radiation for the associated voxel in multiple frames; for each voxel determining a center point in the complex plane; and calculating the arctan of the ratio of the imaginary component and the real component of the difference between the frame value and the center point. Further the step of generating a smooth waveform representing phase changes over time for each voxel may comprise rounding each phase value.

According to other aspects of the disclosure systems are introduced for monitoring life signs in a subject within a target region. Such systems may include: a radar unit comprising: at least one transmitter antenna connected to an oscillator and configured to transmit electromagnetic waves into the target region, and at least one receiver antenna configured to receive electromagnetic waves reflected by objects within the target region and operable to generate raw data; and a processor unit configured to receive raw data from the radar unit and operable to identify oscillating signals therein. The processor unit may include: a frame collator comprising a memory unit configured to store a series of complex frame values for each voxel within the target region; a voxel segmentation module comprising a processor configured to geranate a smooth waveform representing phase changes over time for each voxel; a breathing parameter determination module; and a heart rate parameter determination module. Optionally, the heart rate parameter determination module comprises a signal filter module and a correlation module.

Optionally, the system includes an elevated radar unit directed at a target region; and a seat positioned such that the upper torso of a subject seated thereupon is in situated within the target region. The seat may be positioned such that the back of the subject faces the radar based remote heart rate monitor. Optionally, the seat is positioned such that the chest of the subject faces the radar based remote heart rate monitor.

Where appropriate, the heart rate monitor comprises: a radar unit directed at a target region, a foot rest positioned such that the upper side of a foot of a subject placed thereupon is in situated within the target region.

Additionally or alternatively, the remote heart rate monitor comprises: a first radar unit directed at a target region; and a second radar unit directed at the target region.

In some examples, the signal filter unit comprises a line segment approximation module and a high pass filter module. Optionally, the signal filter unit comprises a delta file generation unit configured and operable to: obtain a set of phase values associated with energy reflected from a selected voxel of the target region at a set of sequential timeframes; create a delta file by subtracting from phase value at each timeframe, the phase value of the previous time frame; and subtract the moving average of the phase values.

BRIEF DESCRIPTION OF THE FIGURES

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the various selected embodiments may be put into practice. In the accompanying drawings:

FIGS. 3A-F indicate examples of plots of series of complex values representing reflected radiation at single voxels within a target region over multiple frames;

FIGS. 14A and 14B are graphs of a section of a periodic signal indicating thresholds and extreme points which may be used in the calculation of slope start and slope end points;

DETAILED DESCRIPTION

Figure 1A:
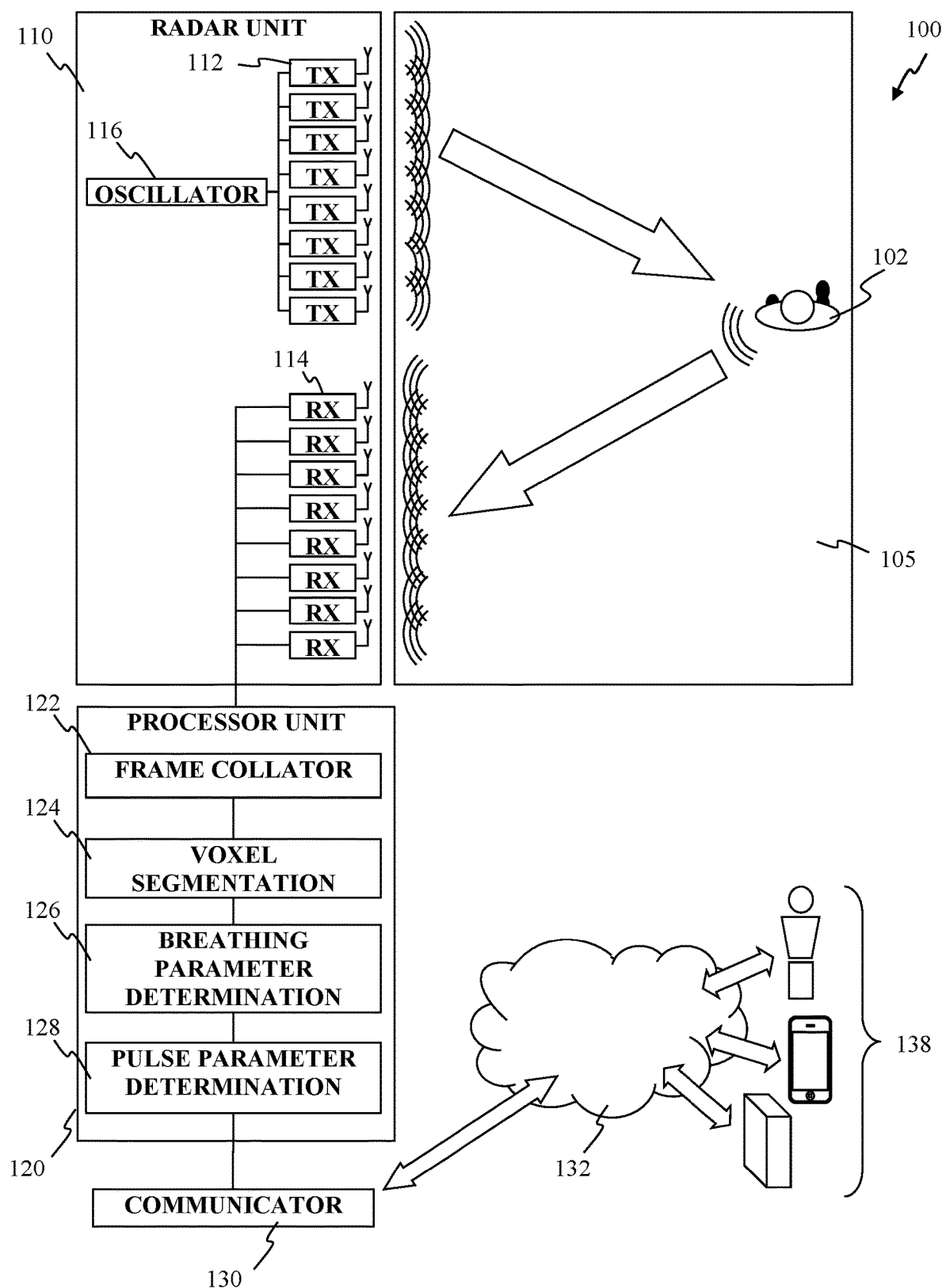
FIG. 1A is a schematic representation of a possible life signs monitor and communication system.

Aspects of the present disclosure relate to system and methods for monitoring the life signs of individuals by using millimeter-wave radar. Systems and methods are described herein for tracking the displacement of body parts during to the breathing cycle. The displacement pattern may be analyzed to extract breathing characteristics and to identify heart rate and pulse patterns.

It is particularly noted that tracking such displacement during the breathing cycle may be used to monitor physiological parameters during sleep time, and/or during wake time. In addition, breathing tracking can be used to identify humans and other targets and their posture for additional radar applications, like falling detection.

As required, detailed embodiments of the present invention are disclosed herein; however, it is to be understood that the disclosed embodiments are merely examples of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally, or alternatively, the data processor may access a non-volatile storage, for example, a magnetic hard-disk, flash-drive, removable media or the like, for storing instructions and/or data.

It is particularly noted that the systems and methods of the disclosure herein may not be limited in its application to the details of construction and the arrangement of the components or methods set forth in the description or illustrated in the drawings and examples. The systems and methods of the disclosure may be capable of other embodiments, or of being practiced and carried out in various ways and technologies.

Alternative methods and materials similar or equivalent to those described herein may be used in the practice or testing of embodiments of the disclosure. Nevertheless, particular methods and materials are described herein for illustrative purposes only. The materials, methods, and examples are not intended to be necessarily limiting.

Reference is now made to FIG. 1A which is a schematic representation of a life signs monitor 100, in accordance with one embodiment of the invention. The life signs monitor may include a radar unit 110, a processor unit 120 and a communication module 130. It is noted that the processor unit 120 may include a breathing characteristic determination module 126 operable to extract breathing data, and pulse determination module 128 operable to extract heart rate data.

The radar unit includes an array of transmitters 112 an array of receivers 114. An oscillator 116 may be connected to at least one transmitter antenna or an array of transmitter antennas. Accordingly the transmitters 112 may be configured to produce a beam of electromagnetic radiation, such as microwave radiation or the like, directed towards a monitored region 105 such as an enclosed room or the like. The receivers 114 may be operable to receive electromagnetic radiation reflected from a subject 102 within the monitored region 105.

Figure 1B:
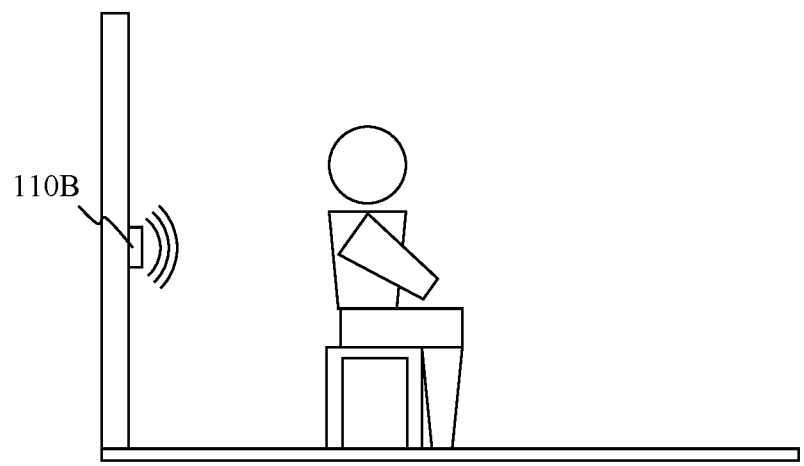
FIGS. 1B-D show various configurations of devices for directing radar waves towards a subject.
Figure 1C:
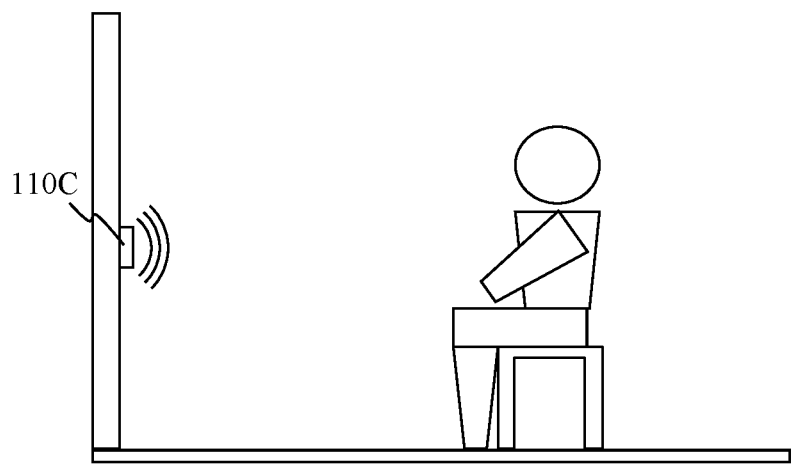
Figure 1D:
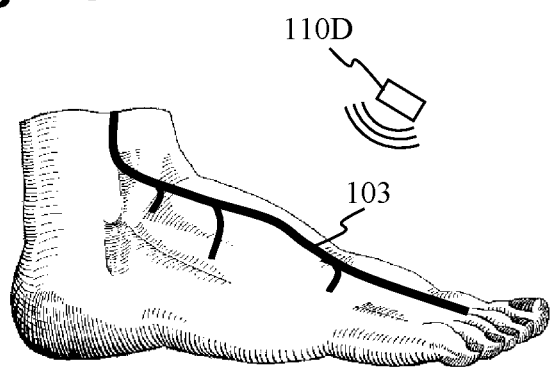
Figure 10:
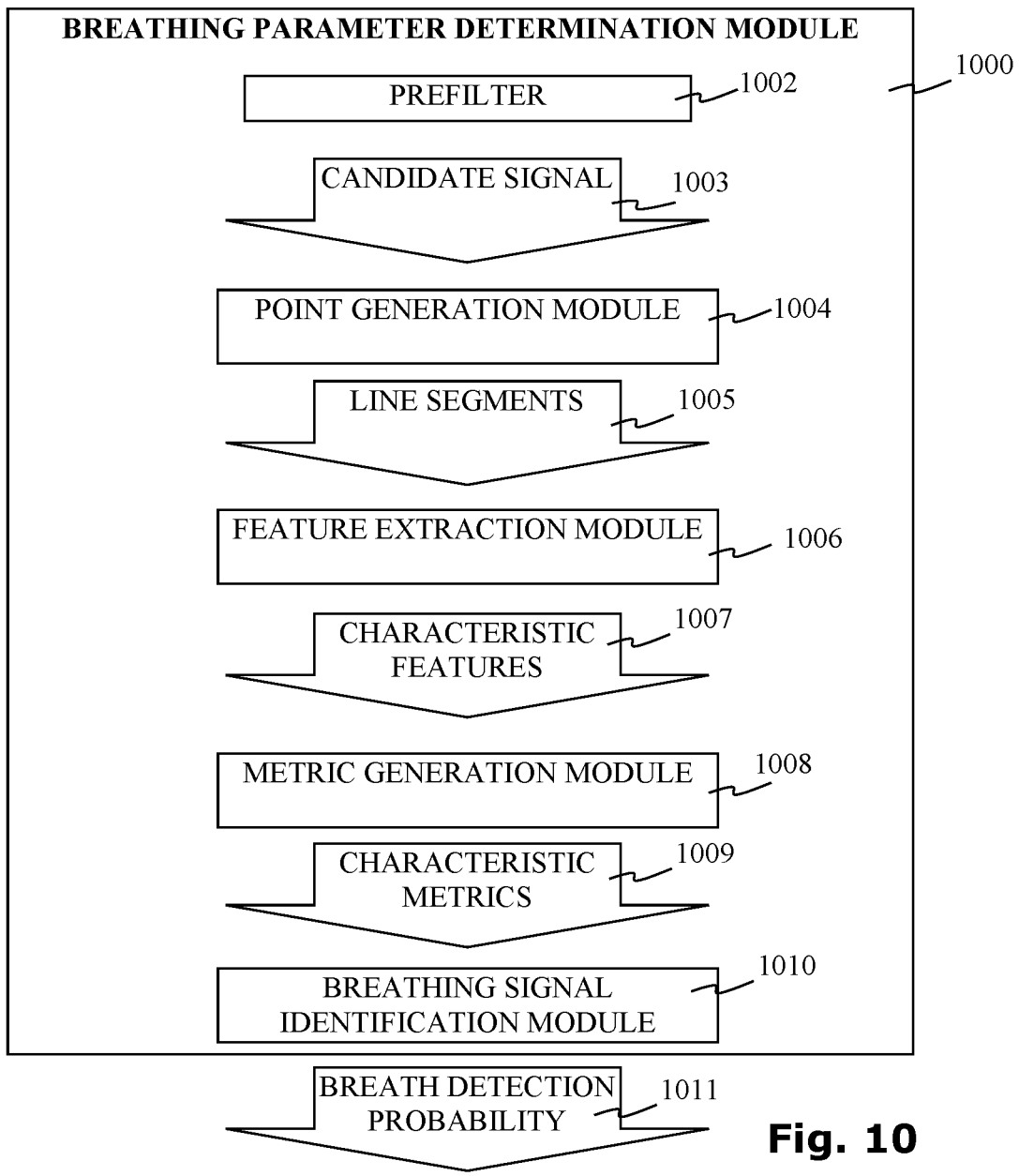
FIG. 10 schematically represents the elements of a breathing parameter determination module configured to process the periodic waveform and to determine probability that the candidate waveform indicates a breathing signal.

It is noted that the subject 102 may variously be standing, sitting, reclining or walking within the monitored region. Where required, for example for sensitive heart rate determination, the subject 102 may sit with his or her back towards the device 110B so that the radiation is directed towards the subject's back, as shown in FIG. 1B. Alternatively, the subject may sit with his or her chest towards the device 110C so that the radiation is directed towards the subject's chest, as shown in FIG. 10. As another alternative, the device 110D may be configured such that radiation may be directed towards the top of the subject's foot, as shown in FIG. 1D where it may receive strong reflections from the dorsal artery 103 for example. Still other systems may use multiple transceivers as described herein below in relation to FIGS. 4A and 4B.

The processor unit 120 may include modules such as a frame collator 122, a voxel segmentation module 124, a breathing parameter determination module 126, and a heart rate parameter determination module 128. Accordingly, the processor unit 120 may be configured to receive raw data from the radar unit 110 and operable to generate breathing parameters and pulse parameters based upon the received data.

The communication module 130 is configured and operable to communicate the pulse parameters to third parties 138. Optionally the communication module 130 may be in communication with a computer network 132 such as the internet via which it may communicate alerts to third parties for example via telephones, computers, wearable devices or the like.

Figure 2:
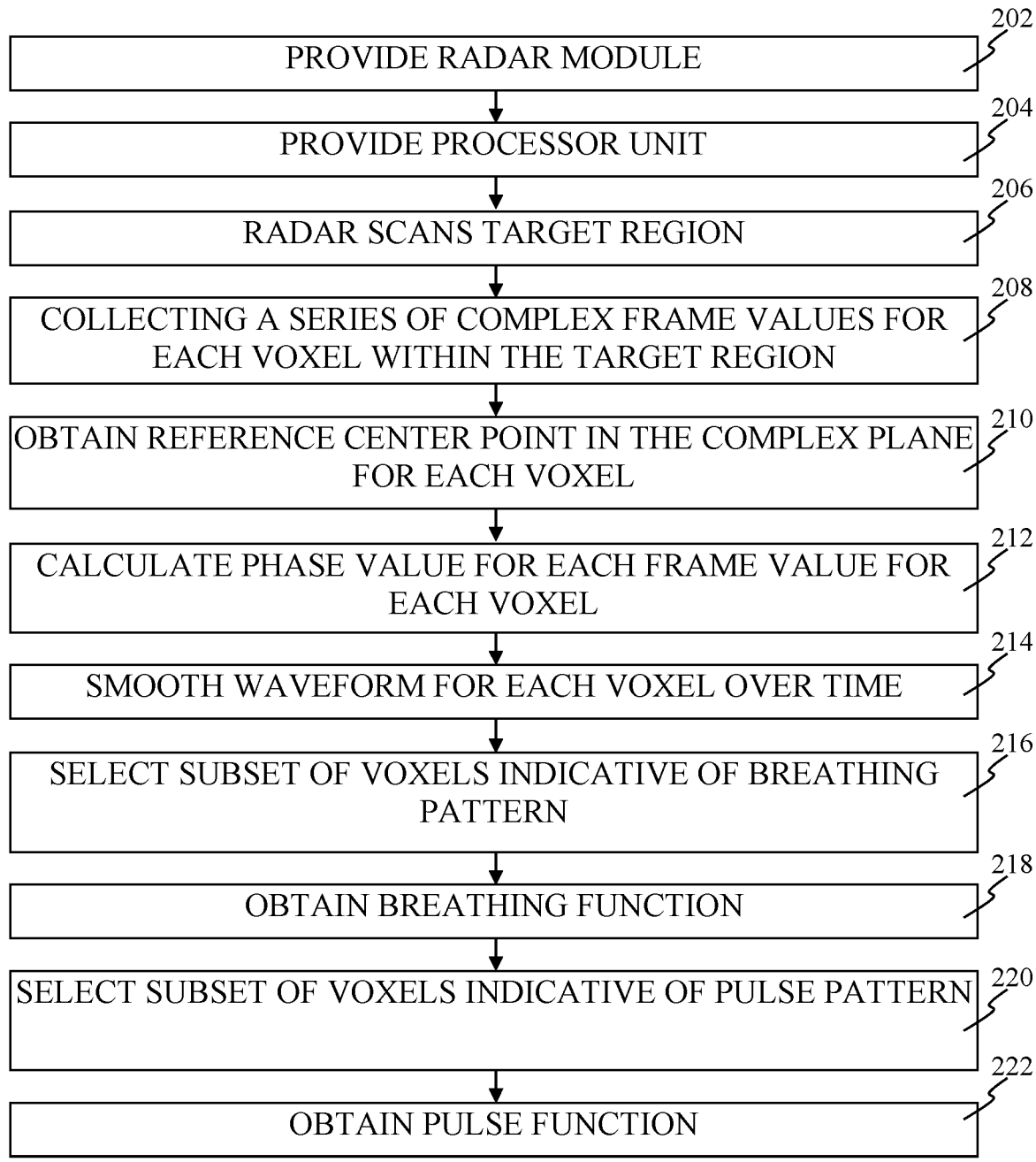
FIG. 2 is a flow chart representing actions of a life signs monitoring method.

Referring now to the flowchart of FIG. 2, selected steps are presented in a possible method for determining breathing parameters within a target region.

The method includes identifying at least one heart rate pattern within a target region by providing a radar unit 202, providing a processor unit 204, the radar transmitting and receiving scanning radiation over the target region 206, the processor unit collating a series of complex values for each voxel representing reflected radiation for the associated voxel in multiple frames 208; for each voxel determining a center point in the complex plane 210; determining a phase value for each voxel in each frame 212; generating a smooth waveform representing phase changes over time for each voxel 214; selecting a subset of voxels indicative of a breathing pattern 216; and determining a breathing function for the detected breathing pattern 218; selecting a subset of voxels indicative of a pulse pattern 220; and determining a pulse function for the detected pulse pattern 222.

The radar unit may include at least one transmitter antenna connected to an oscillator and configured to transmit electromagnetic waves into a monitored region, and at least one receiver antenna configured to receive electromagnetic waves reflected by objects within the monitored region and operable to generate raw data. The processor unit is typically configured to receive raw data from the radar unit and operable to obtain breathing parameters and pulse parameters from the raw data.

Optionally, the processor may generate a series of frames, where each frame comprises an array of complex values representing radiation reflected from each voxel of the target region during a given time segment.

In one embodiment, the method of the invention monitors over a time period a plurality of voxels in parallel. The signal received by the receiver may be given by:

$$s_v[n] = A_v + R_v \cdot \exp\left(j\phi_v + j\frac{4\pi}{\lambda} B_v w[n]\right) + v_v[n]$$

where v is an index of the voxels, n is a time index, $A_v$ is the DC part of the voxel, due to leakage and static objects, $R_v$ is the amplitude (or radius) of the phase varying part of voxel v, $\phi_v$ is a nuisance phase offset of the voxel v, $\lambda$ is the wavelength, $B_v$ is the effective displacement magnitude of the voxel v, $v_v[n]$ is additive noise, and w[n] is the waveform at time n.

For each monitored voxel, the reference center point $\hat{A}_v$ is calculated. By way of illustration, a center may be determined according to a linear-mean-square-error estimator of circle center. For example, estimation may be based on moments of the real and imaginary parts of the received signal. The moments can be averaged with an infinite impulse response (IIR) filter. The forgetting factor of the IIR filter has an adaptive control that balances between the need to converge quickly to a new value upon a change in the environment (e.g. movement of the subject) and the need to maintain consistency of the estimation.

A phase value for each voxel in each frame may be determined by the processor collating a series of complex values for each voxel representing reflected radiation for the associated voxel in multiple frames; and for each voxel determining a center point in the complex plane; and calculating the arctan of the ratio of the imaginary component and the real component of the difference between the frame value and the center point.

Accordingly, given a reference center point, the phase of a voxel v at a given time instant n may be calculated as:

$$\theta_v[n] = \angle(s_v[n] - \hat{A}_v) = a\tan 2(\mathcal{J}\{s_v[n] - \hat{A}_v\}, \mathcal{R}\{s_v[n] - \hat{A}_v\})$$

In order to create a smooth waveform representing phase changes over time, phase values may be rounded. The phase may be unwrapped to generate a smooth waveform without discontinuities greater than $\pi$ according to the formula:

$$\theta_v[n] = \theta_v[n] + 2\pi \cdot \text{round}\left(\frac{\theta_v[n-1] - \theta_v[n]}{2\pi}\right)$$

In another embodiment, phase un-wrapping may be based on prediction of the next phase based on a few previous phases. Such a prediction may be used to lower frame rates and/or improve the resilience to noise while avoiding cycle slips. For example, the following predictor tends to account for phase momentum:

$$\hat{\theta}_v^{Opt2}[n] = \theta_v[n] + 2\pi \cdot \text{round}\left(\frac{(1+\alpha) \cdot \hat{\theta}_v^{Opt2}[n-1] - \alpha \cdot \hat{\theta}_v^{Opt2}[n-2] - \theta_v[n]}{2\pi}\right)$$

where $0<\alpha\leq 1$ is a parameter that controls the weighting of momentum (linear progress of phase) versus stability (zero order hold).

Figure 3A:
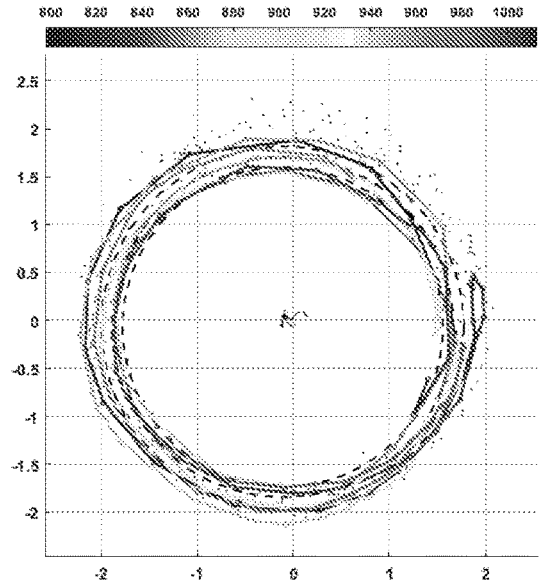
Figure 3B:
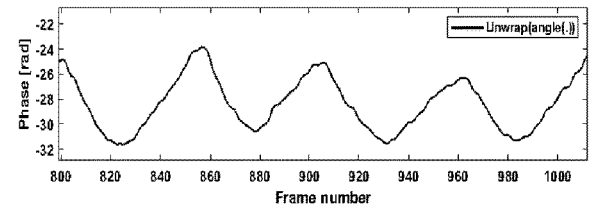
Figure 3C:
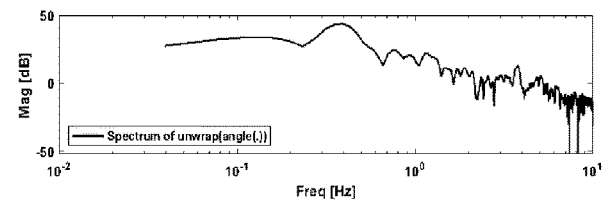
Figure 3C:
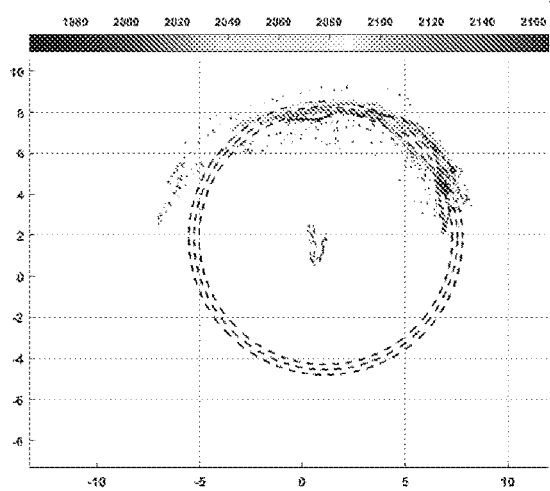
Figure 3E:
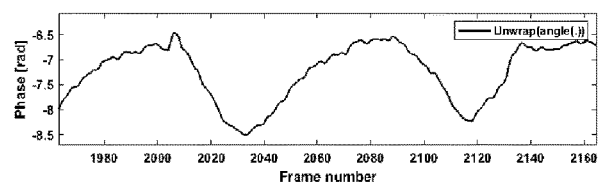
Figure 3F:
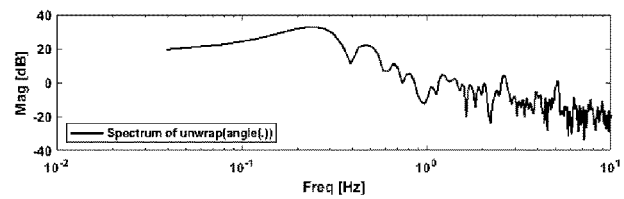

FIGS. 3A and 3D show examples of plots of series of complex values representing reflected radiation at single voxels within a target region over multiple frames. It is noted that the complex values form approximate circles within the complex plane centered at a single point. The periodicity maybe seen over multiple frames giving rise to a characteristic oscillating function such as illustrated in FIGS. 3B and 3E which represent the variation of the phase over time (using frame number as a proxy for time) for the plots of FIGS. 3A and 3B respectively. FIG. 3C and FIG. 3F show corresponding variation in frequency space. Such oscillating functions, may be indicative of breathing or pulse rate for example. The magnetic Referring to Fig.

Voxels indicating breathing characteristics and pulse characteristics may be found, for example, by selecting a subset of voxels conforming to selection rules such as using metrics that evaluate the fitness of those voxels. Such metrics may include fitting to the model of arcs of a circle, fitting to predetermined pattern pulse waveform with strong periodicity and the like, and the spatial location of the voxels.

In many cases, the voxels that fit best for breathing tracking are located near the chest and stomach of the breathing person. In other cases, the most adequate selection is other voxels, such as of reflection from walls or ceiling, or movement of other objects due to the breathing.

An arc-fitting metric maybe calculated for the phase values associated with each voxel; and the selected voxels would be those having an arc-fitting metric above a predetermined threshold. For example a metric may evaluate the accuracy of fitting the data to the model described herein. Relative stability may be measured from the distance between the received signal and the estimated reference center point $$r[n]=s_v[n]-\hat{A}_v$$

The metric may be calculated, for example, as:

$$\text{var}(\hat{\theta}_v[n]) \cdot \frac{\bar{r}^2}{\text{var}(r)}$$

Additionally or alternatively, a time dependency function may be calculated for the phase values associated with each voxel; and voxels may be selected which have periodic characteristics indicative the pulse, such as the duration systole, the duration of diastole, pulse rate and the like as well as combinations thereof.

Such a metric may evaluate the fitness of the un-wrapped phase $\theta_v[n]$ as a clean pulse waveform. A Fourier transform of this signal may be calculated, and it may be checked that the peak value is achieved at a frequency within the range of reasonable periods expected for breathing or of a normal pulse, and that the energy of this peak divided by average energy in other frequencies.

By way of examples periodic characteristics indicative of breathing may include an inhalation-to-exhalation ratio between say 1:1 and 1:6, a breath rate between say 1 and 10 seconds. Also by way of example, the periodic characteristics indicative of pulse of a subject at rest may include a pulse or heart rate between, say, 45 and 150 beats per minute and a ratio of diastole to systole of about 2:1.

The two metrics above may be smoothed, and then combined into a single metric that represents the fitness of each voxel for extraction of pulse.

In one possible embodiment of this invention, a single voxel is selected for pulse determination, based on the above metrics, with hysteresis to avoid frequent jumping among voxels.

In another embodiment, multiple voxels with high metric values are chosen, and their waveforms are averaged by using SVD (PCA) after weighting by the fitness metric.

Lower frequency oscillations of the phase signal indicative of breathing may be filtered out of the phase profile signal to leave the high phase oscillations indicative of the heart rate.

In still other embodiments, Voxel selection may use further metrics such as signal quality (SNR) to validate that the signal extracted from this voxel would have good enough signal to be useful and Breathing detection to validate that the signal observed is consistent with a real breathing signal. These two metrics may be combined to determine that the voxel is suitable for selection.

Figure 4A:
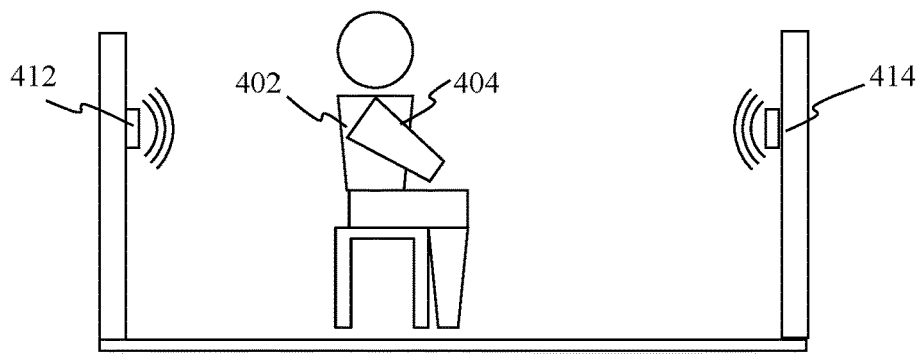
FIGS. 4A and 4B show a system configured to direct radar waves from two units directed towards a subject from different directions.
Figure 4B:
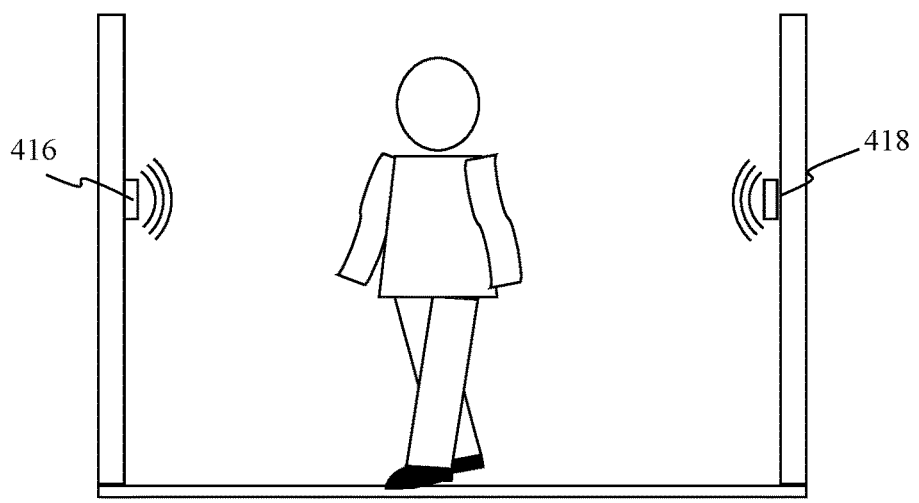

Referring now to FIGS. 4A and 4B a system is illustrated which is configured to direct radar waves from two units towards a subject from different directions. The system may include dual or multiple transceivers in which radiation is directed to the subject's back and chest. It is noted that breathing produces more exaggerated movements in the chest than in the back. Accordingly, where appropriate, the chest directed transceiver may be used to detect oscillations indicative of breathing and the back directed transceiver may be used to isolate the heart rate signal. Moreover, it has been found that that using multiple transceives methods may be executed to isolate heart rate heart rate signals from breathing signals as described herein.

In particular FIG. 4A shows a system in which a back sensor 412 directed towards the back 402 of a seated subject and a chest sensor 414 directed towards the subject's chest 404. According to various embodiments the sensors 412, 414 may be situated about 90 cm above the floor with the distance between back sensor 412 and the back 402 of the subject may be around 50 cm or so, and the distance between the chest sensor 414 and the chest 402 of the subject may be around 80 cm or so. Other heights may be used to direct radar sensors towards, for example the lower back or the upper back, lower chest and upper chest as required.

Figures 4C, 4D:
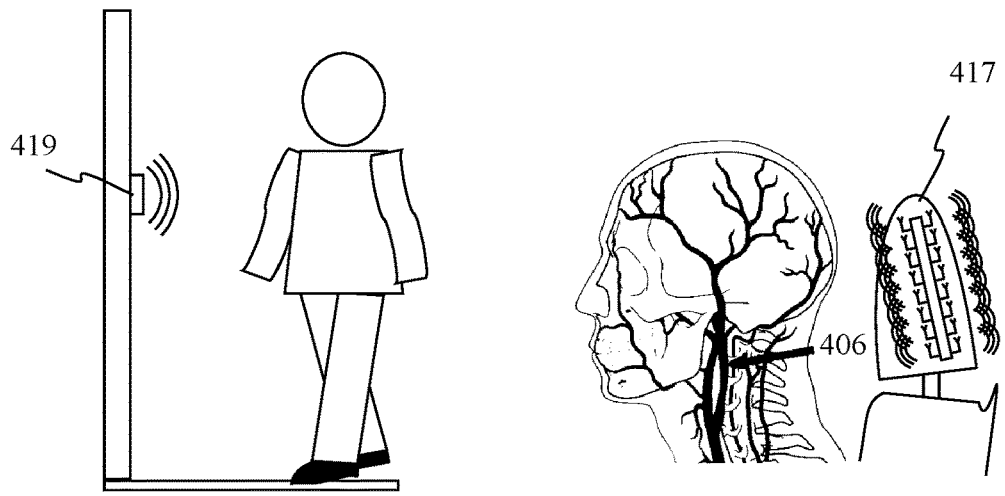
FIG. 4C shows a single chest directed unit for use with a standing subject.
FIG. 4D shows a radar device incorporated into a headrest and directed towards the neck.

As illustrated in FIG. 4C, in still further systems a single sensor 419 may directed towards the subject in a standing position, say at a distance of 40 cm or so.

In particular it has been found that good heart rate signals have been observed when at least one sensor is directed towards the neck and upper back 405 of the subject. This may be due to the strong pulse passing through the carotid artery 406. Accordingly, as illustrated in FIG. 4D, it is noted that a sensor device 417 situated in a head rest of a car may be well positioned to monitor the life signs of the occupant of the car seat. Such a sensor may further monitor the wellbeing and alertness of the driver.

Similar systems maybe arranged with sensors 416, 418 at height of say 150 cm such that they are directed towards the chest and back while the subject is in a standing position such as shown in FIG. 4B.

Figure 5A:
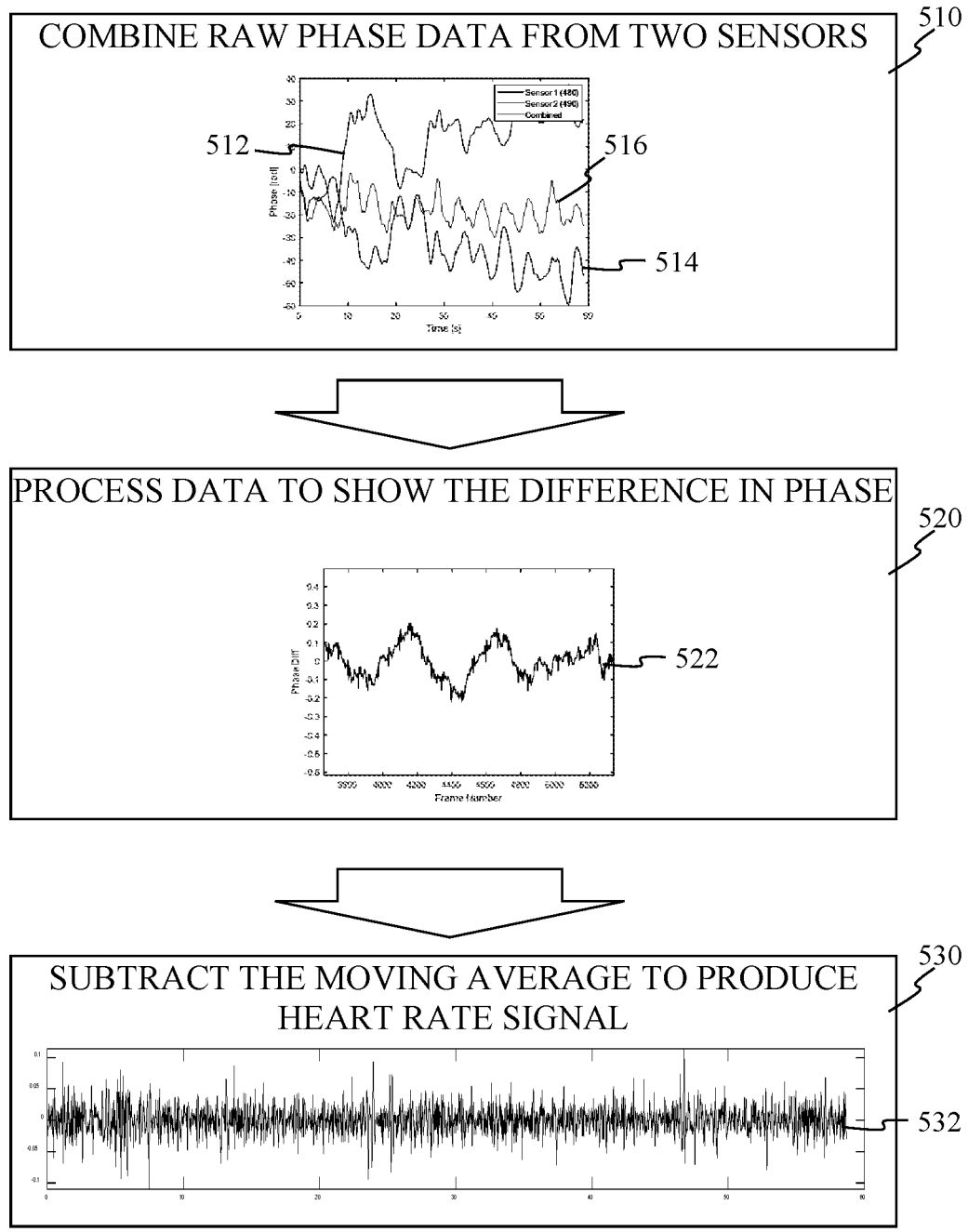
FIG. 5A illustrates some steps in a possible method for processing radar signals obtained in a dual radar system, such as the system shown in FIG. 4D to produce a single displacement signal and isolating heart rate signals therefrom.

FIG. 5A shows a method for processing radar signals obtained in a dual radar system, such as the systems shown in FIGS. 4A and 4B. In one embodiment, in an optional first step, the two obtained phase signals may be combined 510, for example, by adding the two phase signals. When the phase signals. 512, 514 from two transceivers are added, radial variation of phase is often cancelled out. Thus, since breathing generates radial movement of the body, oscillations in the remaining signal 516 are indicative of the pulse.

Alternatively, a single sensor may be used to produce a single phase signal which may be processed to isolate the pulse.

A delta process may be applied to the combined signal 520, or alternatively the single phase signal, in which the phase difference between each pair of consecutive phase values in the combined signal is calculated. This produces a derivative displacement curve 522 which can then be smoothed. For example, smoothing can be achieved by generating a moving time window, and the average value of the displacement curve in the time window can be subtracted from the phase difference at the center of the window 530. Accordingly a Heart Rate Signal 532 may be isolated.

Figure 5B:
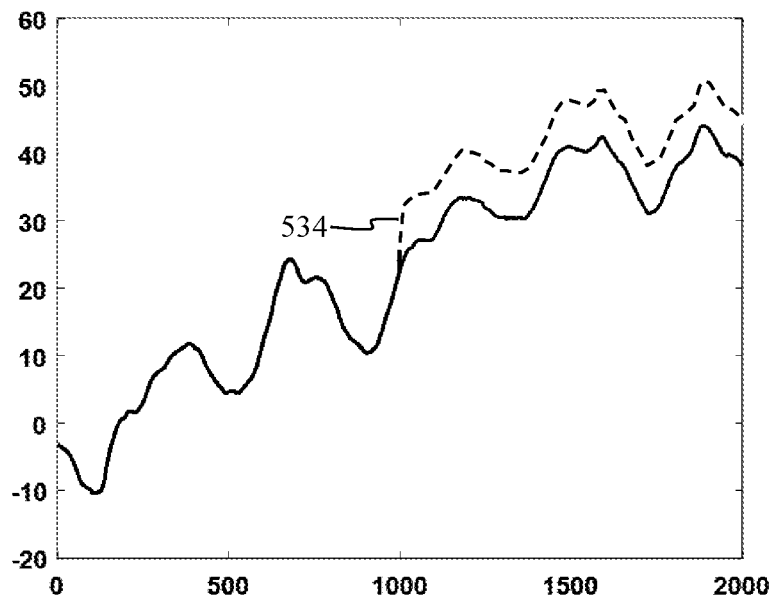
FIG. 5B is a graph illustrating an example of a spiked signal due to a moving subject.
Figure 5C:
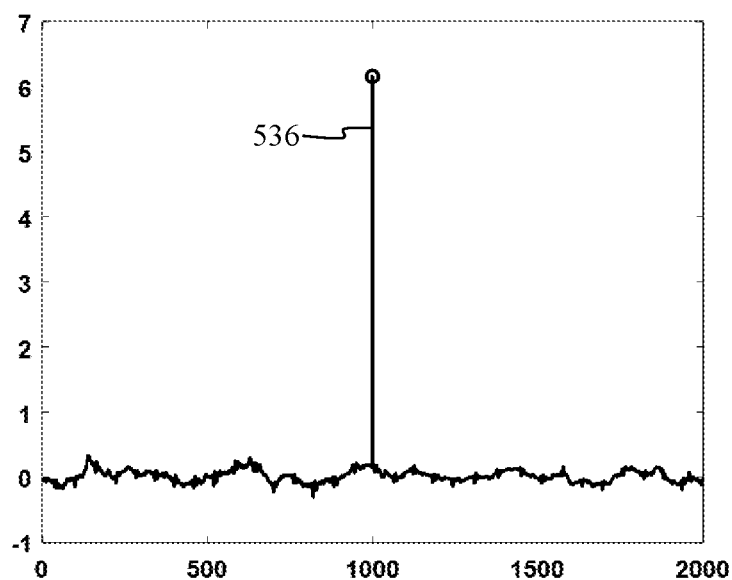
FIG. 5C is a graph illustrating the standard deviation from the average for each frame corresponding to the signal of FIG. 5B.

It is noted that where required, for example where movement of the subject results in direct current fluctuations creating spikes 534 in the signal, such as indicated in FIG. 5B a spike removal mechanism may be applied to the resulting Heart Rate Signal 532 to filter spikes. One example of a spike removal mechanism may be a filter of any data lying beyond a threshold of the environmental median or a certain number of standard deviations from the average values such as indicated in FIG. 5C, in which a clear spike 536 is evident in standard deviation corresponding to the jump 534 at frame 1000 in FIG. 5B.

A jump removal algorithm may be based on a relatively small number of sliding window, of say 9 samples or so, such that for every sample i (the window is centred around the point) in signal $$d_i = X_i - X_{i-1}$$

where X is the input signal, the following metrics are calculated:

$\sigma_W$—the standard deviation of the values in the window W.

$M_W$—median value in the window W.

If the sample $d_i$ satisfies the following conditions, it is replaced by the previous sample to remove the jump:

$$\begin{cases} |d_i| > SF \cdot \sigma_W + |M|_W \\ |d_i| > |M|_W + A \end{cases}$$

where SF is a relative threshold and A is an absolute threshold on the displacement difference.

Figure 5D:
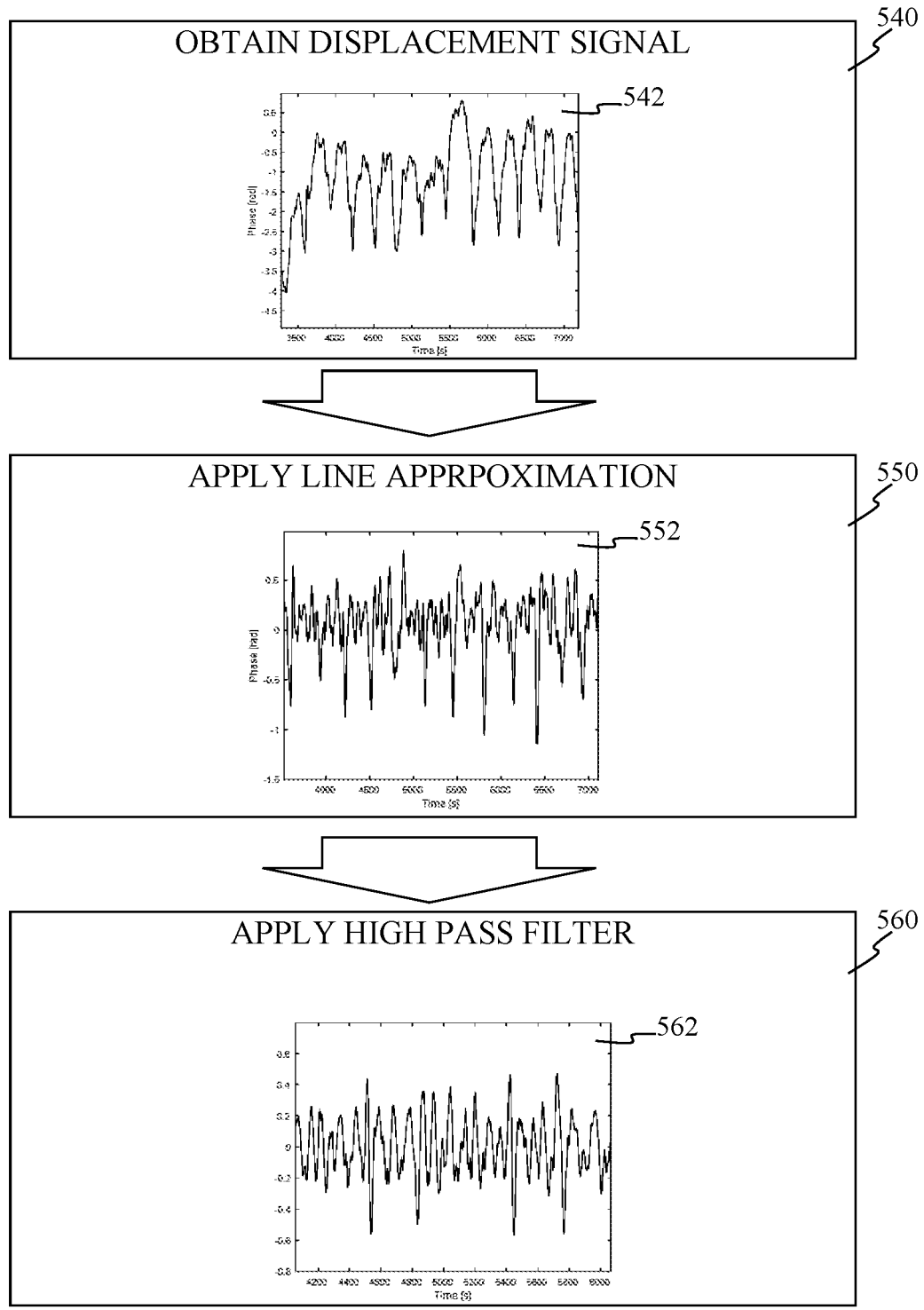
FIG. 5D illustrates another method for isolating heart rate signals from a displacement signal.

Another method for processing the displacement signal is shown in FIG. 5D. A displacement signal 542 is obtained 540 and a line segment approximation is applied to the displacement signal 550. The resulting signal 552 may be subtracted from the displacement signal 542 in order to remove drift in the signal which may be due to respiratory movements. The signal can then be subjected to high-pass filtering 560 to remove respiratory components thereby obtaining an isolated signal 562.

Figure 6A:
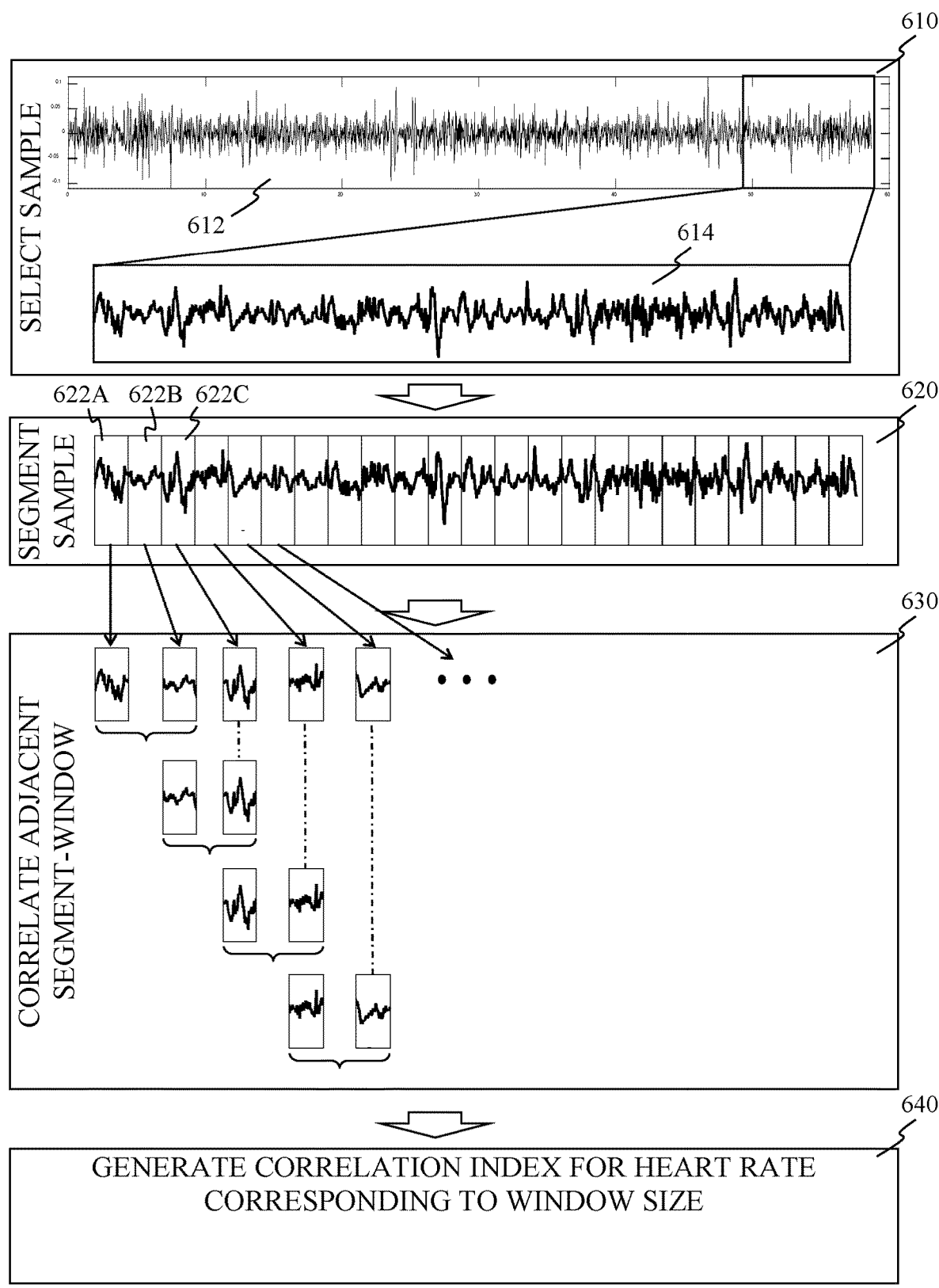
FIG. 6A shows a possible method for generating a correlation index for a heart rate signal corresponding to a particular heart rate.

Reference is now made to FIG. 6A which illustrates a possible method for generating a correlation index indicating the likeliness of a heart rate signal corresponds to a particular heart rate. A selection of the heart rate signal 612 is sampled 610, for example a twelve second sample 614 may be selected for analysis. The sample 614 is segmented 620 into a number of segment-windows 622A, 622B, 622C etc (collectively 622) the duration of which corresponds to a particular heart rate. For example, for a heart rate of 40 beats per minute, a periodicity of 1.5 seconds would be expected, therefore a 12 second segment may be divided into 8 segment-windows each of duration 1.5 seconds. Adjacent segment-windows may be correlated 630, for example, each of the 8 1.5 second segment-windows 622 may be compared to its adjacent segment-window, say 622A and 622B, 622B and 622C, etc . . . , to assess the degree of periodicity 630. The overall correlation may be recorded as a correlation index 640 for example for the 40 bpm heart rate corresponding to the particular window size of 1.5 seconds.

Figure 6B:
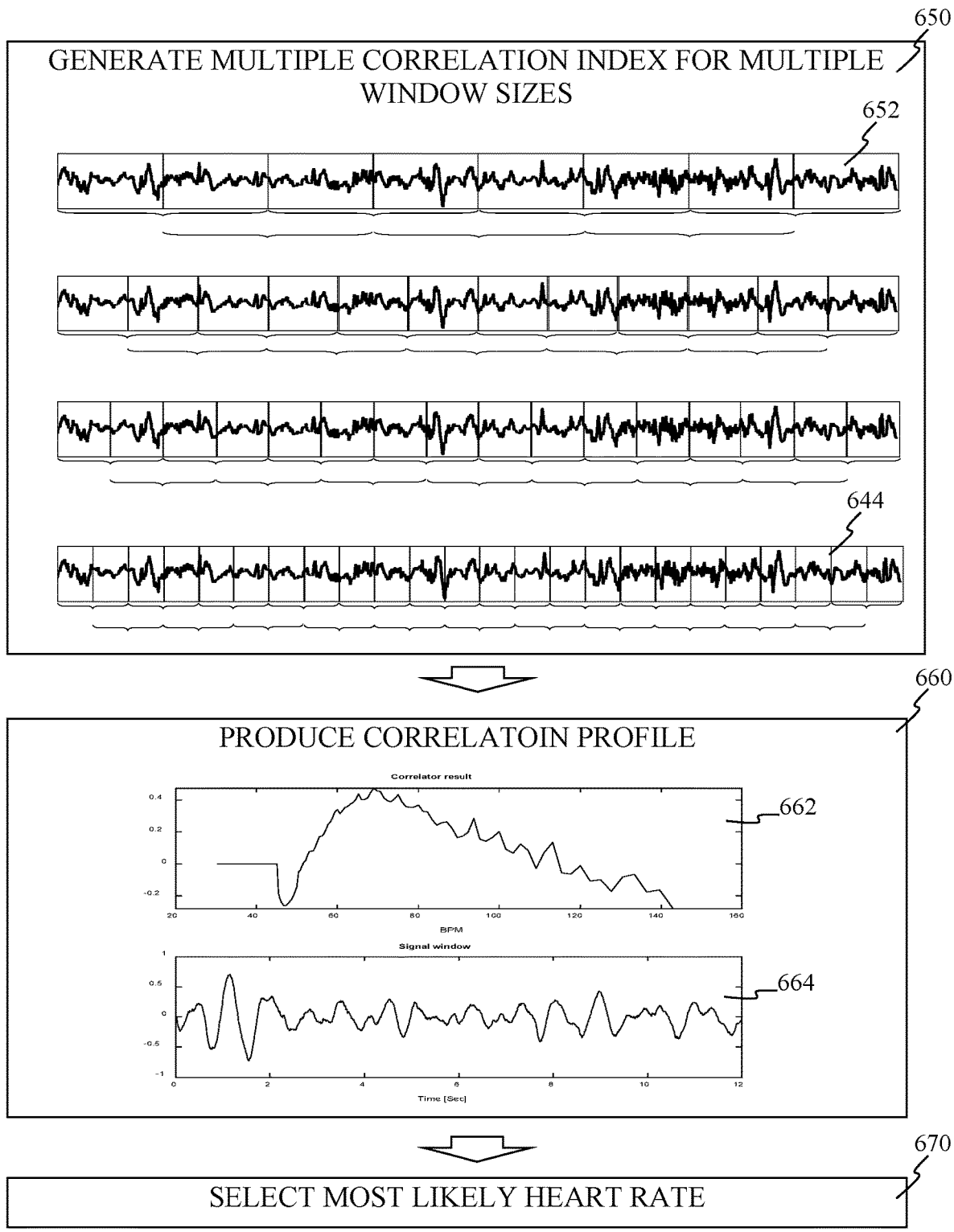
FIG. 6B shows a possible method for generating a correlation profile for a heart rate signal and selecting a likely heart rate.

As indicated in FIG. 6B, correlation indices may be generated for multiple heart rates by segmenting the sample into segment-windows of various lengths 650. Typically, a correlation index is generated for a heart rate of 45 beats per minute, by dividing the sample into a segment-windows of size 1.33 seconds 652 and correlation indices are generated for further heart rates by segmenting the sample with shorter and shorter windows until, say, a segment-window of length 0.6 seconds which corresponds to a heart rate of 100 beats per minute or a segment-window of length 0.43 seconds which corresponds to a heart rate of 140 beats per minute 654. It will be appreciated that other ranges of heart rate may be correlated as required.

Typically, for each integer heart rate between a maximum value max_BPM and a minimum value min_BPM a correlation window $W_{BPM}$ may be defined. Accordingly a segment window of $T_{DET}$ seconds may be divided into $N_{BPM}$ segment-windows $w_{BPM,i}$. Thus for each heart rate candidate hypothesised we the number of correlation windows are $$N_{BPM} = \frac{T_{DET}}{W_{BPM}}.$$

The correlation between each pair of consecutive windows $w_{BPM,i}$ and $w_{BPM,i-1}$ may be calculated to get the a confidence metric such as:

$$C_{BPM} = \sum_{i=2}^{N_{BPM}-1} corr(w_{BPM,i}, w_{BPM,i-1})$$

After calculation for all candidate heart rates values the multiple correlation indices may be plotted on a graph 662 to produce a correlation profile 660 characteristic of the signal 664. The peak of this profile may be used to indicate the most likely heart rate of the monitored individual. Accordingly, the most likely heart rate corresponding to the signal my be selected 670. Accordingly the heart rate may be selected to be the value of:

$$\overline{BPM} = \mathrm{argmax}(C_{BPM})$$

with a confidence given by the autocorrelation $$\mathrm{Conf} = \max(C_{BPM})$$

It is further noted that the characteristic correlation profile thus produced may itself serve as a novel diagnostic metric in its own right.

Figure 6C:
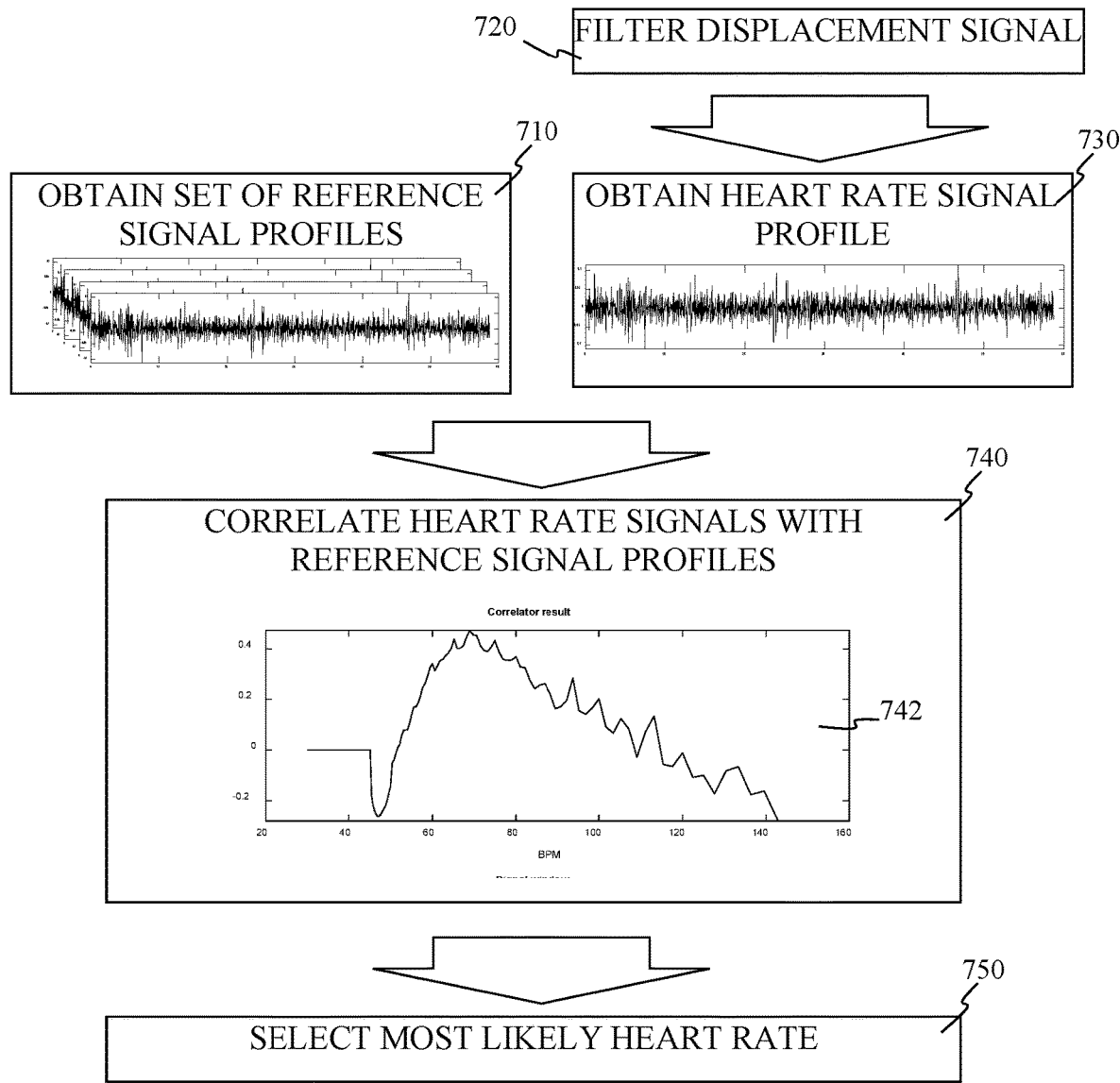
FIG. 6C shows an alternative method for generating a correlation profile and selecting a likely heart rate.

FIG. 6C shows another method for determining a heart rate from the displacement signal generated by subtracting the moving average, as explained above. The method shown in FIG. 6C utilizes two or more reference profiles 710. In the generation of each reference profile, a subject is exposed to the radiation from a dual transceiver system as explained above. Simultaneous with the exposure to the radiation, the heart rate of the subject is determined by any known method. For example, the heart rate may be determined by obtaining an electrocardiogram of the individual or a sonogram may be obtained by placing a microphone on the subject's chest over the heart. The reference signal is processed as explained above in reference to FIG. 5A to produce the reference profile. Thus, each reference profile has an associated heart rate.

Referring still to FIG. 6C, a displacement signal obtained on a subject can be filtered 720 using a high-pass filter. Thus a heart rate signal may be obtained for the subject 730. The heart rate signal may bed analyzed by generating a cross-correlation of the filtered signal with each of the reference profiles 740. A reference profile 742 having maximum correlation with the subject's displacement signal is selected, and the heart rate associated with the reference profile of maximum correlation is determined to be the subject's heart rate 750. Validation rules may be applied such that only likely heart rates are selected.

The RPM may be determined by finding the maximal value of the unwrapped phase fast fourier transform (FFM).

$$\widehat{BPM} = \mathrm{argmax}(FFT((\theta - \bar{\theta}) \cdot W_{Hamming}))$$

A hamming window may be used to reduce sidelobes.

It is further noted that a high pass filter may be used to cancel patient movement. Accordingly, in order to support various breathing frequencies a bank of Moving Average based (MA subtraction) high pass filters may be introduced, for example a 10 second average corresponding to an RPM of 6, a 5 second average corresponding to an RPM of 12, a 3 second average corresponding to an RPM of 20, a 1 second average corresponding to an RPM of 60, or such like.

Figure 7:
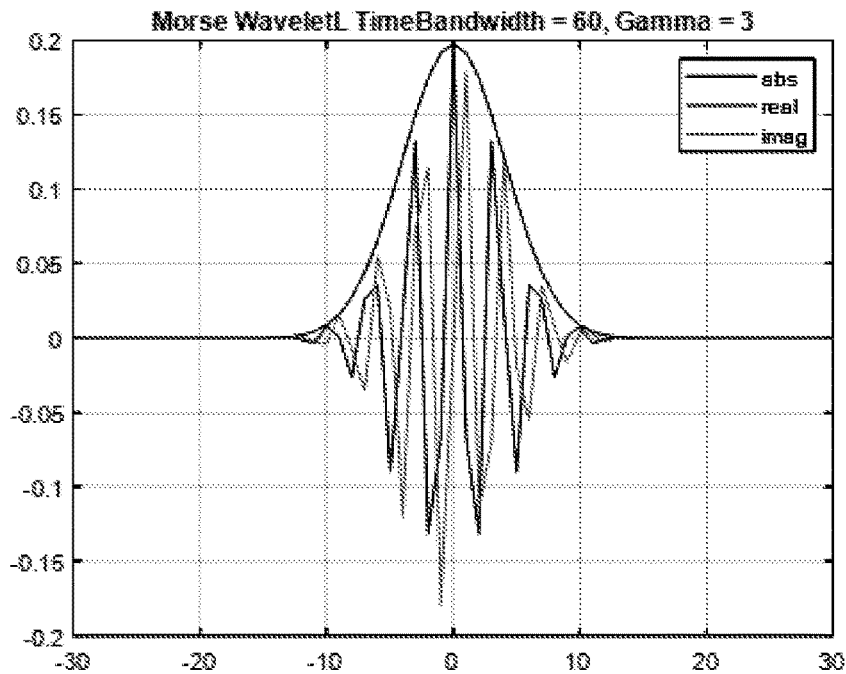
FIG. 7 shows an example of a possible Morse wavelet used for estimation of RPM.

RPM estimation may be performed using a Continuous Wavelet Transform. In the example of FIG. 7 a Morse wavelet with Time-BW Product of 60 and symmetry parameter γ=3 is used.

The continuous wavelet transform yields a scalogram S and each scale corresponds to a pseudo-frequency $F_a$, which may be given by:

$$F_a = \frac{F_c}{a}$$

where a is the scale and $F_c$ is the wavelet central frequency.

The maximal pseudo-frequency in the centre of a measurement interval T corresponds to the estimated RPM $$\widehat{RPM} = \mathrm{argmax}\left(S\left([F\_min, F\_max], \frac{T}{2}\right)\right) * 60$$

and the confidence may defined by $$\hat{C} = \max\left(S\left([F\_min, F\_max], \frac{T}{2}\right)\right)$$

It is noted that because the scales are selected according to the length of the signal the wavelet cannot be scaled to be longer than the signal. Therefore lower frequencies may require longer signals. Accordingly, in order to measure slow RPM, a longer recording is needed.

Best voxel selection may be performed by picking the combination of voxel candidates coupled with the high pass filter length that yield the best confidence.

Since filter length affects RPM accuracy and also the breathing waveform quality the system can be configured to prioritize certain filter lengths over others by adding a filter length dependent penalty $[P_{L1}\ P_{L2} \ldots P_{LM}]$ to the confidence matrix rows accordingly. This can help improve accuracy in certain ranges.

Referring back to the breathing signals of FIGS. 3B and 3E, it is noted that it has been surprisingly difficult to identify breathing signals by detecting peaks in the signal. Peak detection has been surprisingly unsuccessful due to factors such as false negatives associated the lack of periodicity of real breathing signals, and false positives associated with phase jumps, sweeping, random walk data caused by phase wrapping at high energy in low frequency signals. Therefore, a more robust method for breathing signal determination is desirable.

Accordingly, an extracted periodic waveform signal may be processed by a line segmentation mechanism to determine if the periodic waveform signal is consistent with the characteristics of a breathing signal.

Figure 8:
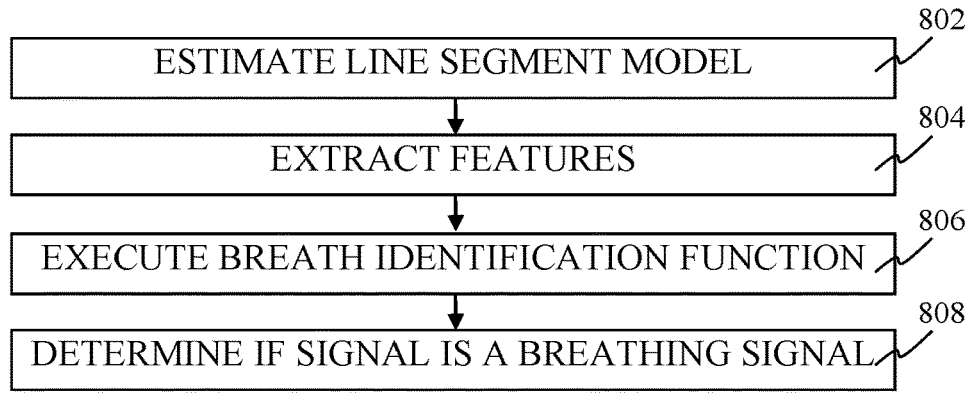
FIG. 8 is a flowchart representing a possible method for determining if a candidate periodic waveform is consistent with the characteristics of a breathing signal.

Referring now to the flowchart of FIG. 8, a line segmentation mechanism may be operable to execute a method by estimating a line segment model (LSM) for a candidate waveform 802, extracting characteristic features from the line segment model 804, executing a breath identification function 806 and determining a probability that the candidate waveform is a breathing signal 808.

Figure 9:
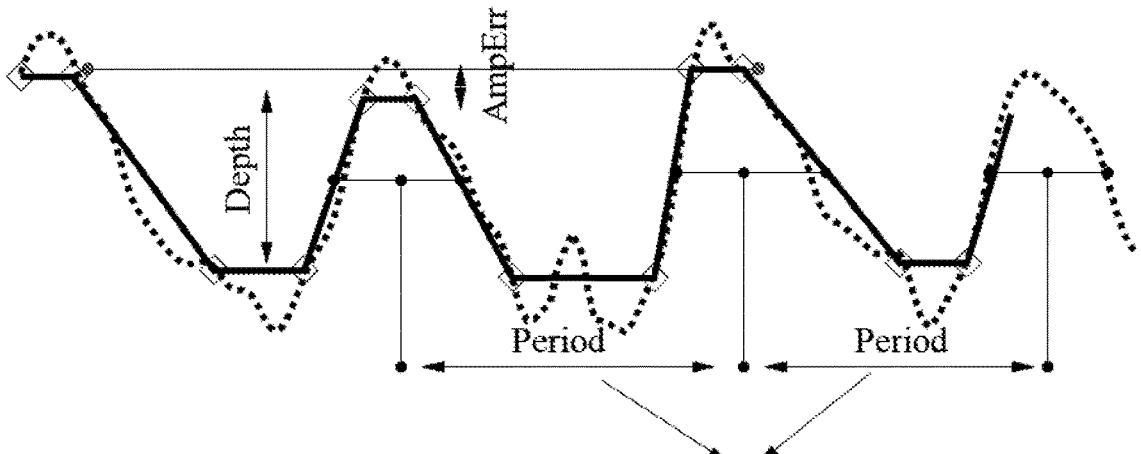
FIG. 9 is a graph indicating how a Line Segment Model comprising a series of trapezoid sections may represent a periodic signal.

With reference now to FIG. 9, a line segment model of a candidate signal is characterized by four line segments for each period. Various features such as depth, amplitude and period may be determined for each trapezoid cycle of the LSM. Accordingly characteristic features such as average depth, amplitude error, average period, period variation and the like may be determined for the candidate signal. These features may be converted into metrics suitable for determining the probability that the signal represents a true breathing signal.

It is noted that advantages of the LSM include its modularity and the physical meaning associated with the parameters resulting in certain breathing parameters such as RPM being readily extracted. Moreover, it is easier to explicitly remove trends, the time axis is independent of the RPM as the window of each update is the breathing cycle itself, and the relatively small number of variables for each cycle which simplifies implementation and reduces the memory requirements for storing the signal.

Accordingly, as schematically represented in FIG. 10, a breathing parameter determination module 1000 may include a prefilter 1002, a point generation module 1004, a feature extraction module 1006, a metric generation module 1008, and a breathing signal identification module 1010.

The prefilter 1002 may be configured to provide a candidate signal 1003 to the point generation module 1004. The point generation module 1004 receives the candidate signal 1003 and generates a line segment model (LSM) 1005, typically by identifying a first point and a last point on each significant slope in the candidate signal 1004.

The feature extraction module 1006 is configured and operable to extract characteristic features 1007 from the LSM 1005 such as rate per minute, rate variation, depth variation, slope variation, rest-state amplitude variation, rest-state length variation and the like as described herein.

The metric generation module 1008 is configured and operable to process the features and to calculate characteristic metrics 1009 for each feature indicating the probability that the feature is consistent a breathing signal.

The breathing signal identification module 1010 receives the characteristic metrics 1009 for the features and applies a breathing identification function to integrate the metrics and determine a probability 1011 that the candidate signal represents a breathing signal.

Figure 11A:
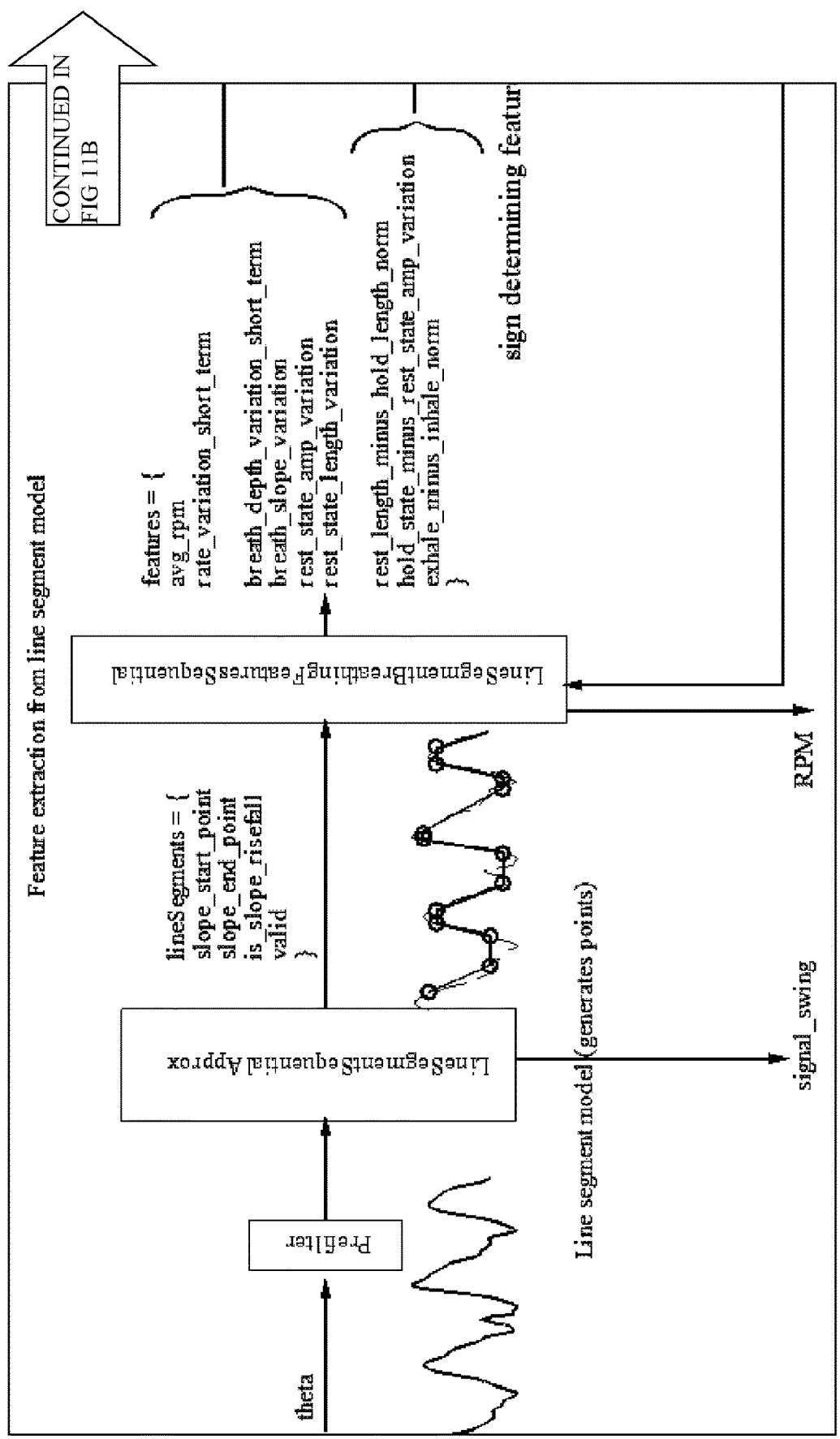
FIGS. 11A-C in combination represent a schematic block diagram indicating how components of the system may combine to process the candidate signal.
Figure 11B:
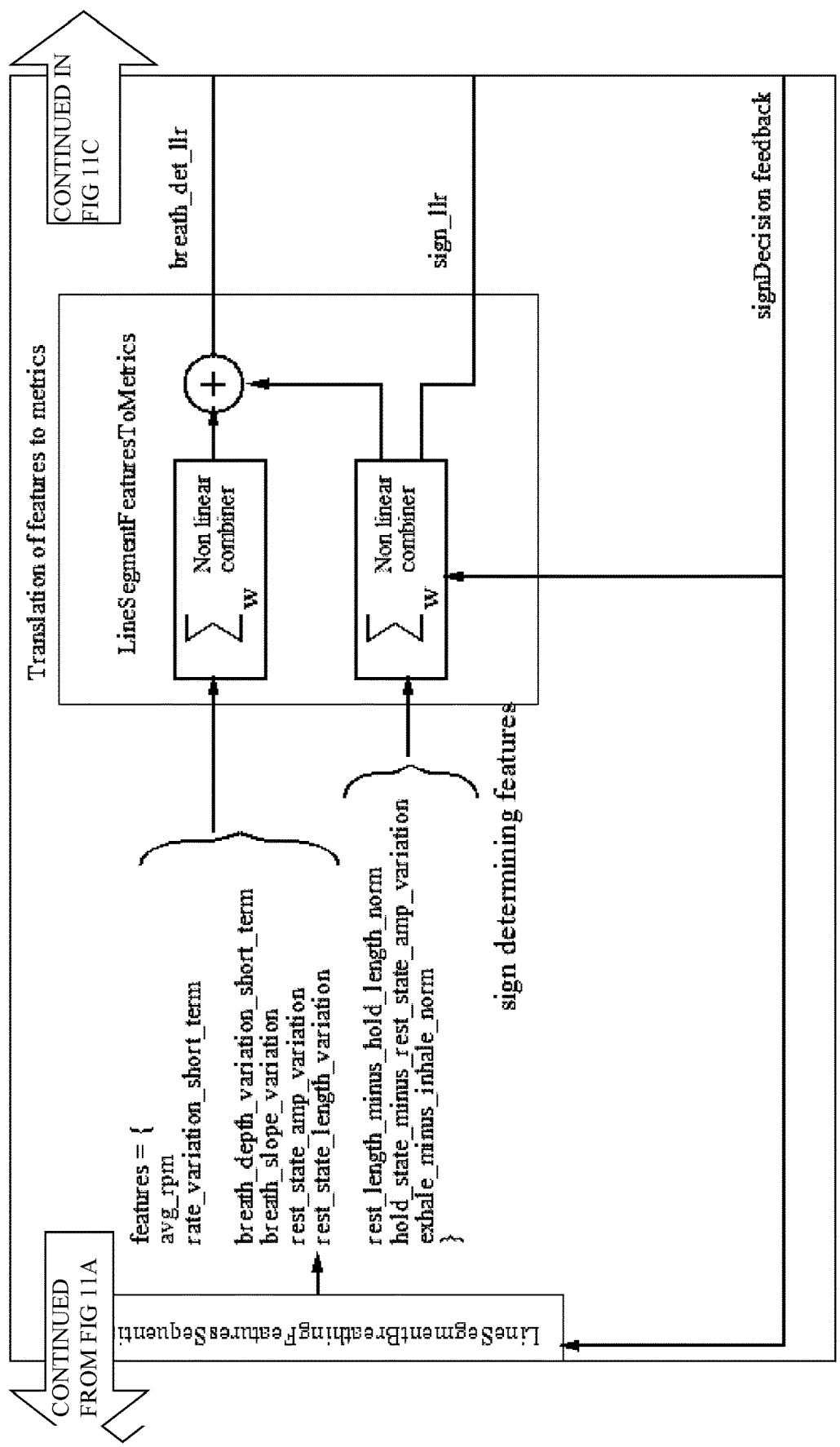
Figure 11C:
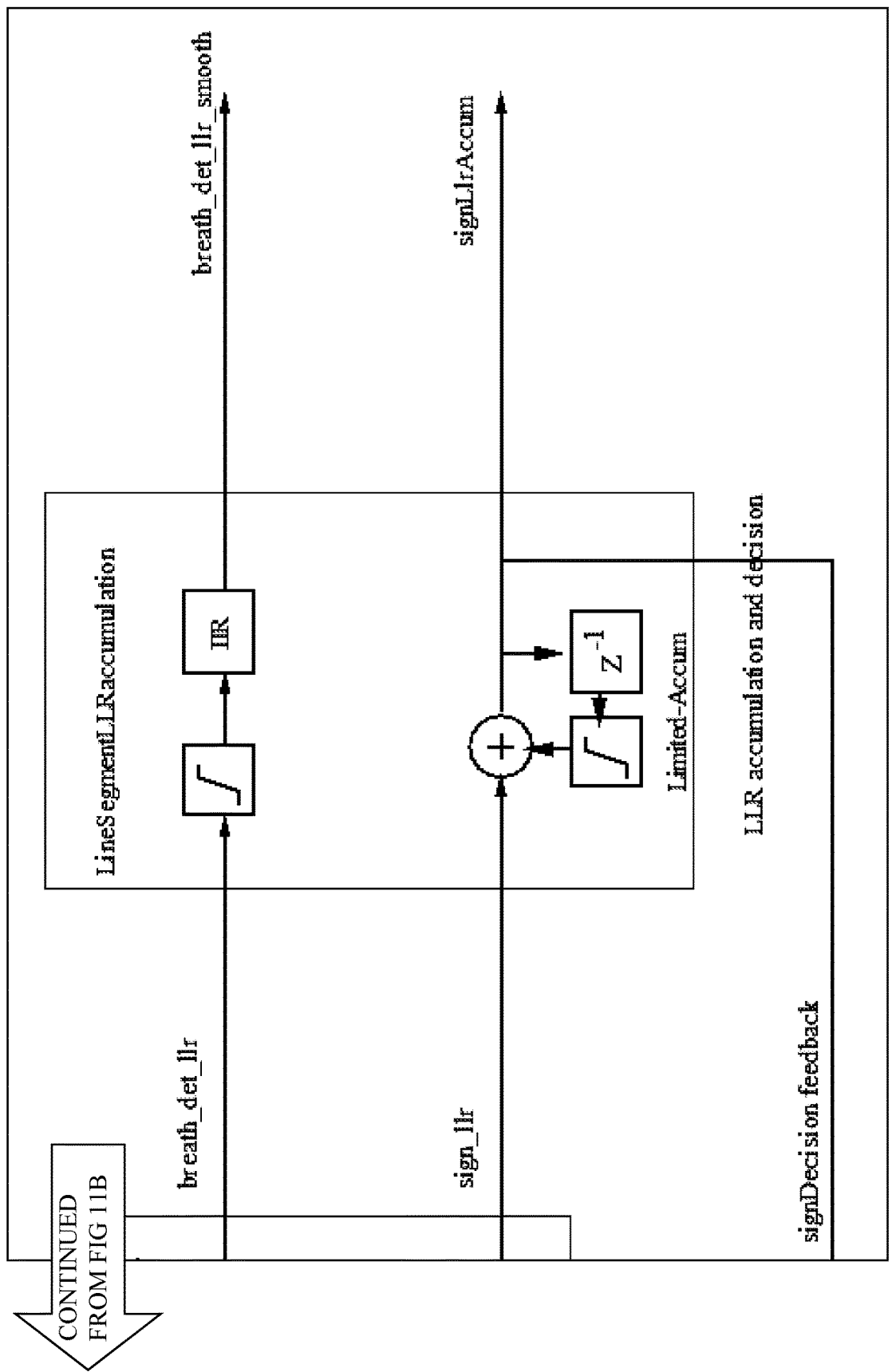

By way of example the block diagram of FIGS. 11A-C indicates how components of the system may combine to process the candidate signal.

The prefilter receives a periodic phase variation signal, for example in order to determine if the voxel from which the phase variation signal is generated is a suitable for monitoring a breathing signal. The prefilter may be used to reduce the level of noise or focus the extracted signal to the frequency domain at which the breathing signal is expected, and extracts a candidate periodic signal which is transferred to the point generation module.

The point generation module may apply a Line Segment Sequential Approximation by identifying the slope_start point and slope_end point for each significant slope in the candidate signal.

Figures 12A, 12C:
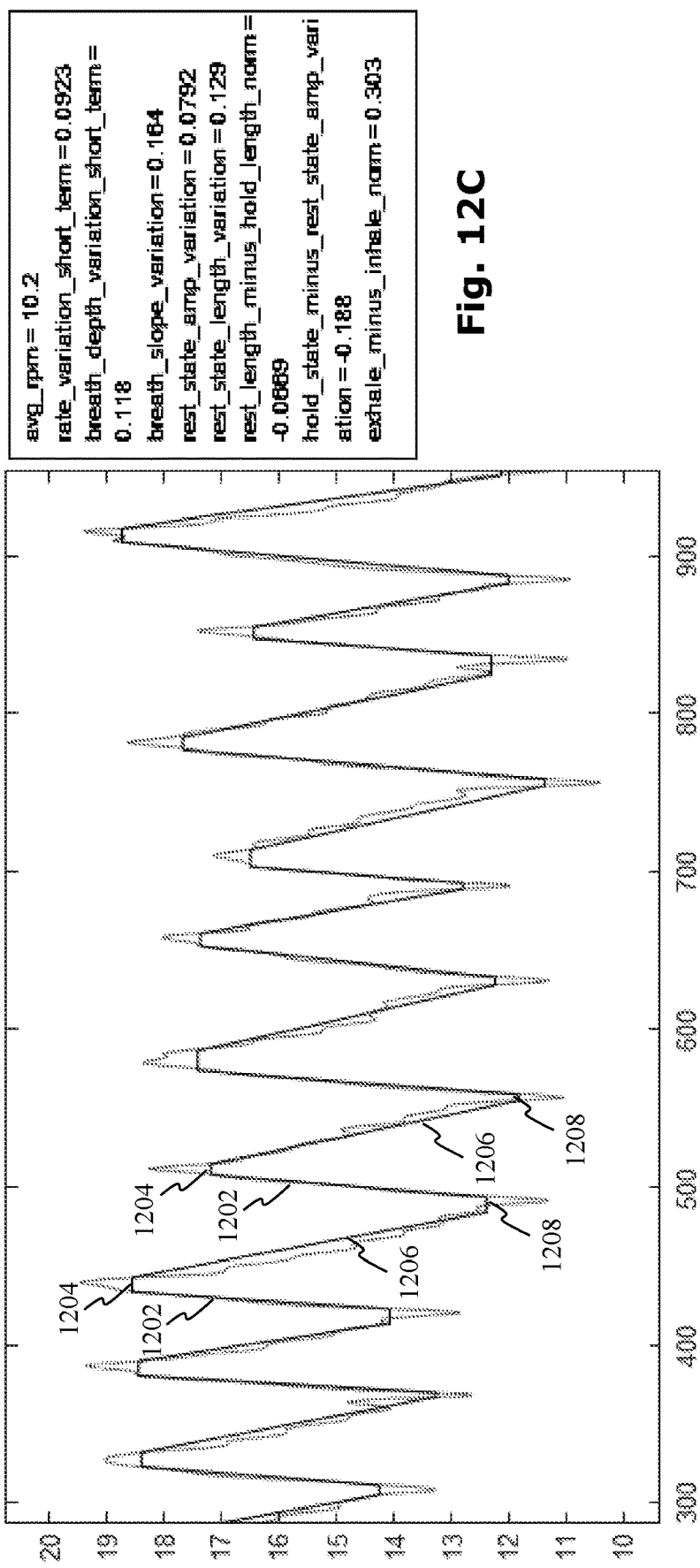
FIGS. 12A and 12B are graphs presenting examples of Line Segment Models superimposed upon the periodic signal from which they are generated.
FIGS. 12C and 12D indicate the characteristic features extracted from the Line Segment Models of the graphs in FIGS. 12A and 12B respectively.
Figures 12B, 12D:
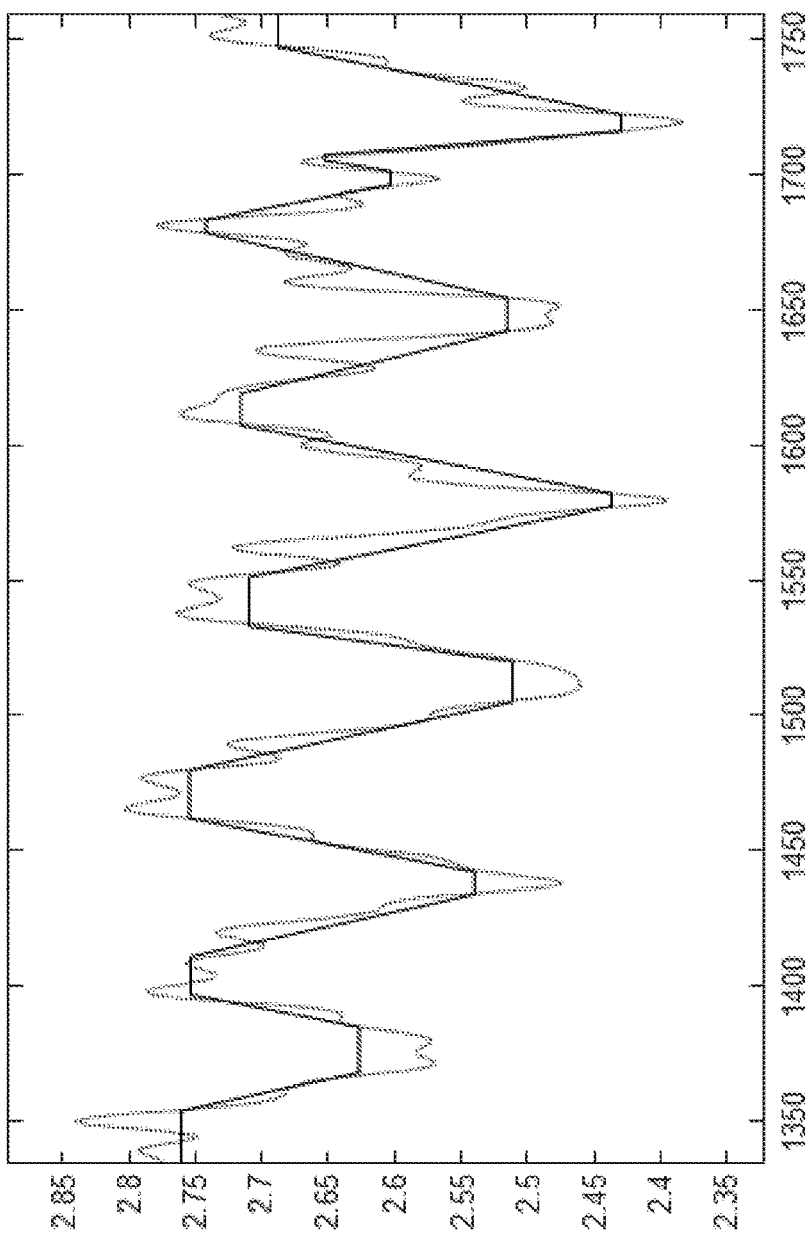

Referring now to the graphs of FIGS. 12A and 12B. Two examples are presented showing Line Segment Models superimposed upon the periodic signals from which they are generated. The input periodic signal is processed so as to generate a Line Segment Model having four line segments for each cycle. The four line segments consist of a rise-segment 1202, having a positive gradient, a hold-segment 1204, which follows the rise-segment and has a zero gradient, a fall-segment 1206, having a negative gradient, and a rest-segment 1208, which follows the fall-segment and has a zero gradient.

Figure 13A:
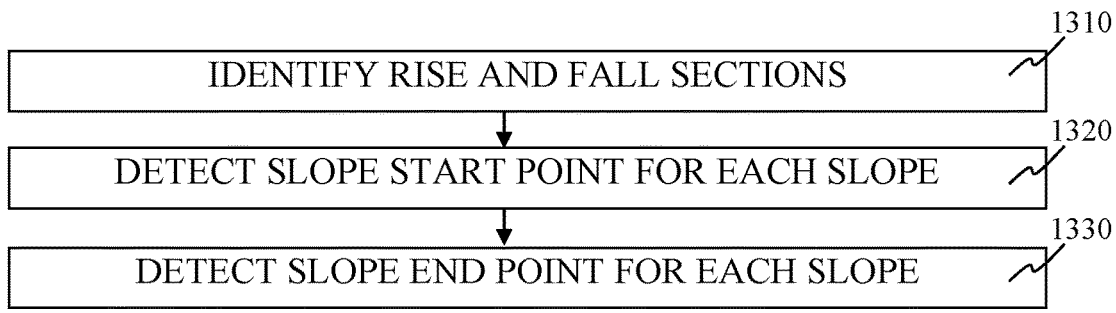
FIG. 13A is a flowchart illustrating the main steps of a method for determining the key points defining the beginning and end of each line segment.

As illustrated in the flowchart of FIG. 13A, the point generation module executes a method to determine the key points defining the beginning and end of each line segment. The method includes identifying significant rising and falling sections within the periodic signal 1310, detecting a slope start point for each significant sloping section 1320, and detecting a slope end point for the each significant sloping section 1330.

Figure 13B:
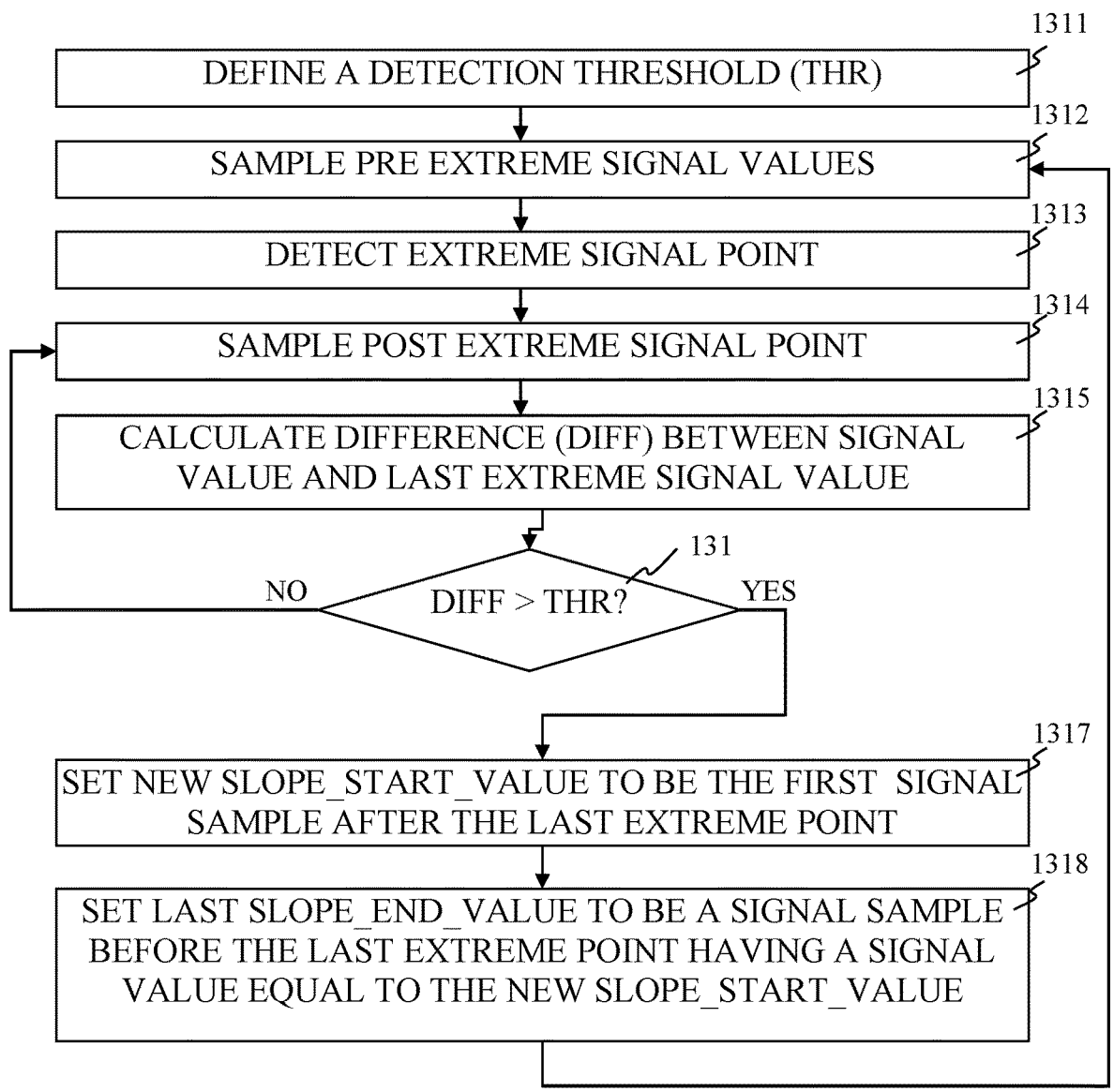
FIG. 13B is a flowchart illustrating a possible method for setting the values of the slope start and slope end points.
Figure 15:
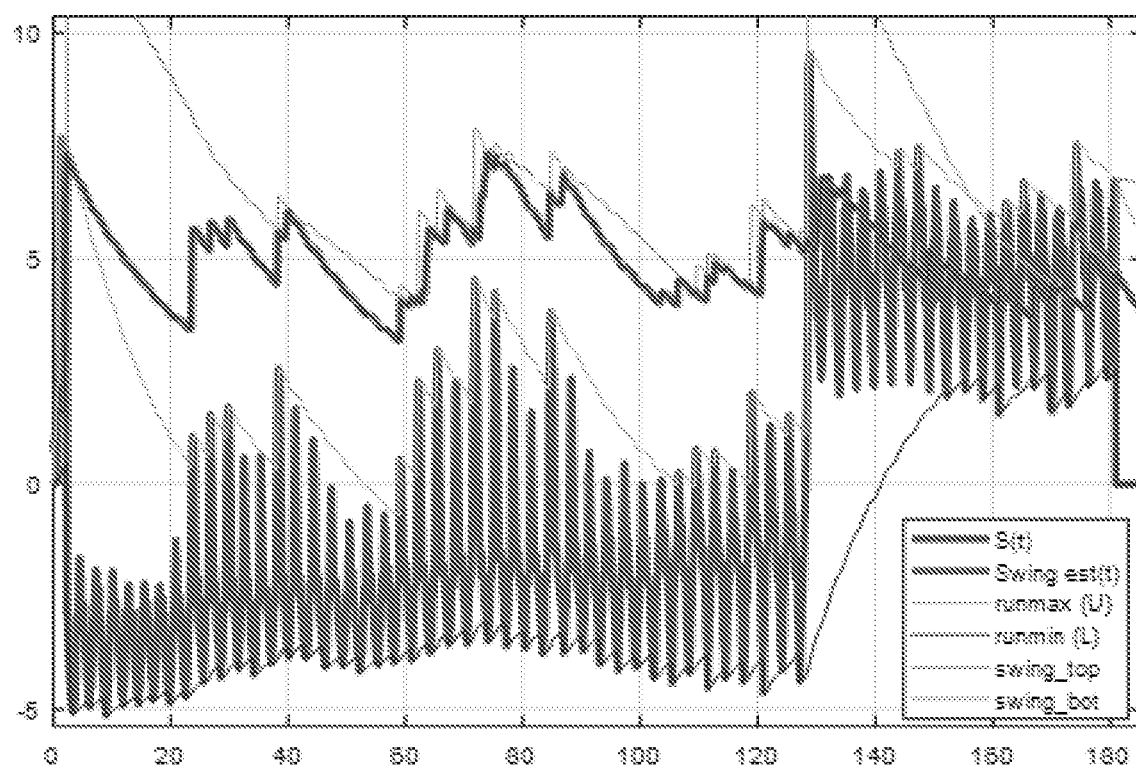
FIG. 15 is a graph illustrating how a swing index may vary over time for a fluctuating signal.

Various definitions may be used to set values for the slope start and slope end points, one such method is illustrated by the flowchart of FIG. 13B. In this method, a detection threshold THR is defined 1311, during a pre-extreme phase signal values are sampled 1312, an extreme signal point is detected 1313 and recorded and a post-extreme phase begins during which signal values are again sampled 1314. During the post extreme phase, the difference DIFF is calculated between each signal value and the last extreme signal value 1315. This difference DIFF is compared to the threshold value THR. If the difference DIFF is greater than the threshold THR then a new slope start point is set for a line segment following the extreme signal point by selecting a slope_start_value point to be the first signal sample after the previous extreme 1317, and a new slope end point is set for a line segment preceding the extreme signal point by selecting the last slope_end_value point to be a signal sampled during the previous pre-extreme phase which has the same value as the new slope_start_value 1319.

The steps of the method may be understood with reference also to FIGS. 14A and 14B. In the method of the example a detection threshold may be selected to a value such that only significant slopes are detected and smaller fluctuations are discarded. Referring particularly to the graph of FIG. 14A showing an example of a section of a periodic signal, the detection threshold risefall_detect_thresh 1402, 1404 is indicated. The detection threshold is measured from the extreme points 1406, 1408 of the signal towards the center and thereby defines an upper margin and a lower margin within which small peaks are not considered significant. By way of example, the graph of FIG. 14A indicates the limits 1402, 1404 of the margins with circular markers.

Referring back to FIG. 13B, the signal is sampled 1312 to detect a local extreme in the signal value 1314, the local extreme 1406, 1408 may be a local minimum 1408 or a local maximum 1406 signal value. Once an extreme signal value is detected, each post extreme sample is analyzed by calculating the value of the difference between the current sample signal value and the last extreme signal 1315. If the absolute value of the difference (DIFF) is smaller than the threshold value (THR) then the next post extreme signal value is sampled.

If the absolute value of the difference (DIFF) is larger than the threshold value (THR) then the slope start point is set 1317, optionally this may be selected as the first signal sample after the last extreme, although other samples may be selected as required. By way of example, the graph of FIG. 14B indicates the slope start points with diamond markers 1410, 1412.

Once the new slope start point is set, the previous slope end point may be determined retroactively to be a point previous to the last extreme which has the same signal value as the new slope start point 1318. The signal is then again sampled to detect the next local extreme. By way of example, the graph of FIG. 14B indicates the slope end points 1414, 1416 with octagonal markers.

It is noted that the signal may undergo swings of various amplitudes and frequencies which due to effects which do not depend upon breathing. These include large shifts in amplitude, possibly due to body movement, phase jumps due to phase unwrapping error, other noise and the like.

Where appropriate, an algorithm may further normalize for swing of the signal, so for example a rise may be identified when the following expression is true (Signal−min(Signal))>(risefall_detect_thresh*Swing), similarly a fall may be identified when the following expression is true (Signal−max(Signal))<(risefall_detect_thresh*Swing).

Where "min" and "max" in the expressions above are measured over the period starting from the previous fall/rise detection respectively.

Swing may be evaluated to identify the overall shape of the signal, and adapt to it. Simple ways to estimate the swing may be by taking the RMS of the signal, measured over a time window, e.g. using an IIR, and multiplying by a factor; or estimating the swing as the difference between the last high and low extremes, e.g. Swing=RunMax($s_n$)−RunMin($s_n$), where RunMax/RunMin are the maximum/minimum over a time window, or approximate forms of these values. A possible implementation of RunMax/RunMin may be defined by the recursive equations below. The relation $y_n \stackrel{\text{def}}{=} \text{RunMax}(x_n)$ is defined by:

$$y_n = (1-\alpha)\max(y_{n-1}, x_n) + \alpha x_n$$

For some constant $\alpha$, and respectively for minimum.

One way to achieve this which may be resilient to unidirectional jump is to evaluate a swing index S where there is a positive peak having two signals smaller by S on one side or both sides as required. For example, one could take max and min over time windows $$p^+[k] = \max_{n \in window[k]}[s_n], \quad p^-[k] = \min_{n \in window[k]}[s_n]$$

and take the swing as the minimum between a "rise" and a "fall": $\min(p^+[k]-p^-[k-1], p^+[k-1]-p^-[k])$.

The swing index may be calculated by measuring the distance between the signal and the upper and lower limits, and taking the side with the minimum distance. Accordingly, the swing may be given by:

$$\text{Swing}=\min(\text{RunMax}(U_n-s_n),\text{RunMax}(s_n-L_n))$$

where $U_n$=RunMax($s_n$) and $L_n$=RunMin($s_n$), and RunMax/Min are defined above, such that, if a sudden rise occurs in the signal's bias, then $U_n$ will track the rise, but $L_n$ will lag behind. The graph of FIG. 11 illustrates how the values of the swing index, then $U_n$ and $L_n$ may vary over time for a fluctuating signal.

Referring back now to the block diagram of FIGS. 11A-C, the point generation module transfers the Line Segment Model to the feature extraction module which may execute a Line Segment Breathing Features Sequential function upon the Line segments to generate breathing signal features for the overall signal. Amongst others, a selection of examples of such features are presented below for illustrative purposes:

avg_rpm—this value may approximate the RPM of a true breathing signal which may be expected to have a value around 3-60, with a typical value of 15. This value may be calculated using the formula avg$_{rpm}$=60/AvgPeriod rate_variation_short_term—this value may indicate the consistency of the breathing rate. This value may be calculated using the formula rate_variation_short_term=PeriodVariation/AvgPeriod breath_depth_variation_short_term—this value may indicate the periodicity of the breathing amplitude. This value may be calculated using the formula breath_depth_variation_short_term=DepthVariation/AvgDepth breath_slope_variation—this value may indicate the periodicity of the breath signal slope. This value may be calculated as the Mean[rise/fall] using the formula breath_slope_variation=SlopeVariation/AvgSlope rest_state_amp_variation—this value may indicate the variation in the rest state amplitude which tends to have lower variation and does not typically depend on depth. This value may be calculated using the formula rest_state_amp_variation=AmpVariation[rest]/AvgDepth rest_state_length_variation—this value may indicate the variation in the rest state duration. This value may be calculated using the formula rest_state_length_variation=LengthVariation[rest]/AvgDepth rest_length_minus_hold_length_norm—this value may indicate how much longer the rest state is than the hold state which for typical breathing should have a positive value. This value may be calculated using the formula rest_length_minus_hold_length_norm=(AvgLength[Rest]−AvgLength[Hold])/avgPeriod hold_state_minus_rest_state_amp_variation—this value may indicate how much more variation there is in the Hold state than the rest state. This is typically a positive value for typical breathing and may be used to compensate for periodicity. This value may be calculated using the formula hold_state_minus_rest_state_amp_variation=(AmpVariation[hold]−AmpVariation[rest])/(AmpVariation[hold]+AmpVariation[rest])

exhale_minus_inhale_norm—this value may indicate how much longer exhalation is than inhalation, exhalation time for typical breathing is typically about double the inhalation time. This value may be calculated using the formula exhale_minus_inhale_norm=(AvgLength[Fall]−AvgLength[Rise])/avgPeriod For the purposes of the above, the terms used are given by:

$$AvgPeriod = \hat{E}[\text{Period}],$$

where $\hat{E}[x]$ denotes running empirical mean.

$$\text{Period} = \frac{1}{F_s}(\text{mean}\,(n_{i-3}:n_i) - \text{mean}\,(n_{i-7}:n_{i-4}))$$

$$PeriodVariation = \hat{E}[|\text{Period} - AvgPeriod|]$$

$$\text{Depth} = s_{2i} - s_{2i-1}$$

$$AvgDepth = \hat{E}[\text{Depth}]$$

$$DepthVariation = \hat{E}[|\text{Depth} - AvgDepth|]$$

$$\text{Slope} = \frac{s_{2i} - s_{2i-1}}{n_{2i} - n_{2i-1}}$$

$$AvgSlope[u] = \hat{E}[\text{Slope} \mid u]$$

$$SlopeVariation[u] = \hat{E}[|\text{Slope} - AvgSlope[u]| \mid u]$$

$$AmpErr = \frac{1}{2}s_i - s_{i-4} + \frac{1}{2}s_{i-8}$$

$$AmpVariation[u] = \hat{E}[|AmpErr|\,u]$$

By way of example, reference is made to FIG. 12C which indicates the characteristic features extracted from the signal shown in FIG. 12A, as well as to FIG. 12D which indicates the characteristic features extracted from the signal shown in FIG. 12B.

It is noted that selected characteristic features may be independent of time-scale and of each other.

Referring again to the block diagram of FIGS. 11A-C, the feature extraction module transfers the extracted characteristic features to the metric generation module which may execute a Line Segment Features to Metrics function to aggregate the characteristic features into metrics.

It will be appreciated that the characteristic features may be categorized into two broad groups, sign-dependent features and sign-independent features.

Sign-dependent features include rest_length_minus_hold_length_norm, hold_state_minus_rest_state_amp_variation, and exhale_minus_inhale_norm. These features may be expected to be positive for any normal breathing signal and inversion of the breathing signal would also invert these features. It would be expected that the higher the value of these features, the more likely the signal is to be a breathing signal. These features may be used in order to determine the sign (inverted/non inverted) of the received signal; after detecting the sign (e.g. by integration of these features over one or more breathing periods), these features may be multiplied by the detected sign in order to align them.

Sign-independent features include avg_rpm, rate_variation_short_term, breath_depth_variation_short_term, breath_slope_variation, rest_state_amp_variation, and rest_state_length_variation. These features are typically independent of inverting the signal.

Accordingly, when translating the features into characteristic metrics a log likelihood ratio (LLR) may be generated to show the probability that the signal is breathing. For example, the probability that a signal is breathing may be given by $$\frac{1}{e^{-LLR}+1},$$

where LLR=log{Pr(breathing)/Pr(~breathing)}.

By way of illustration, a possible method is presented below in which an overall probability may be determined by passing each feature through a piecewise linear function to convert it to LLR, and then summing these LLRs and adding a global offset where applicable.

Figure 16A:
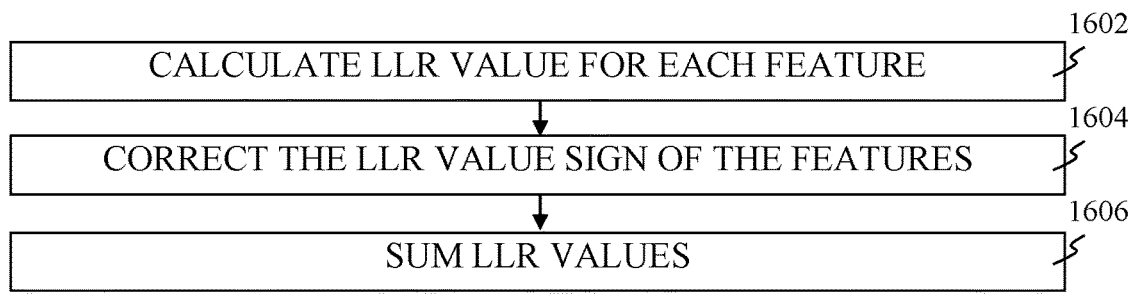
FIG. 16A is a flowchart and FIG. 16B is a schematic diagram illustrating a method for generating feature metrics.
Figure 16B:
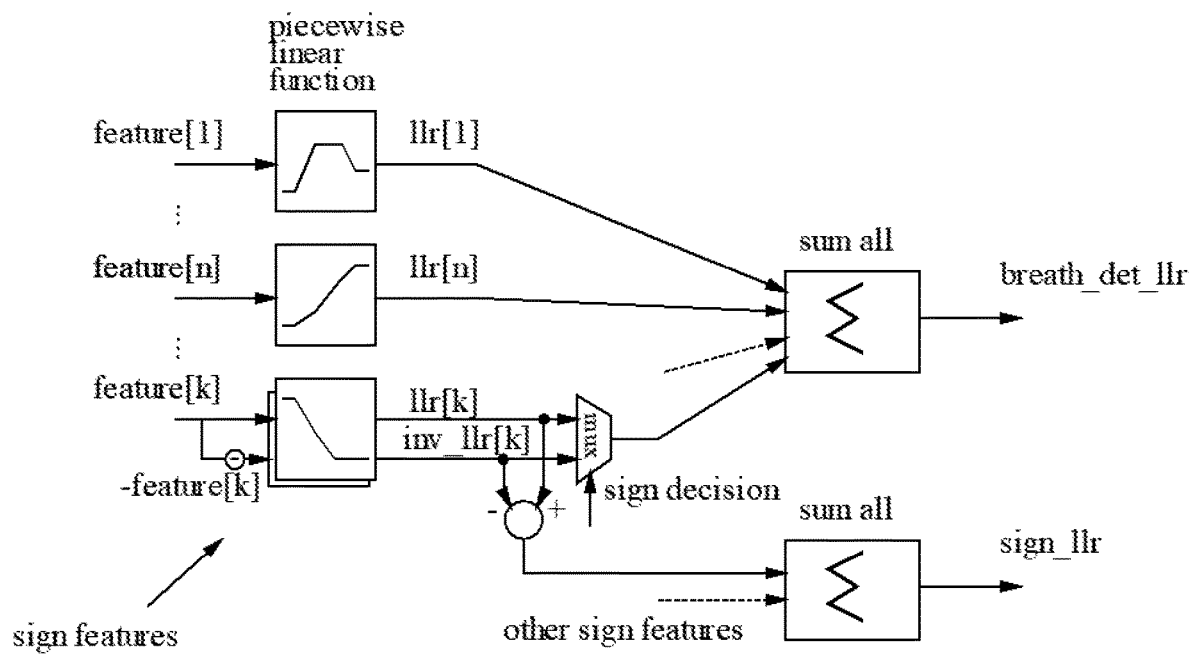

Referring to the flowchart of FIG. 16A and the schematic of FIG. 16B, the method for generating metrics may include calculating an LLR value for each feature 1602, correcting for the sign of the LLR value the features 1604, and summing the corrected LLR values 1606.

The step of calculating LLR per feature may use a piecewise linear function such that, for each feature, a piecewise linear description of the LLR may be provided by a function of the feature, given as a set of points (each point is a set of feature value and LLR value), typically the LLR is a constant below the first point and above the last point.

$$LLR_{perFeature}[n]=\text{interp1}(\text{points}[n], \text{feature}[n])$$

Because, for the sign related features, inversion of the signal means inversion of the feature, an LLR may be calculated for the two hypotheses: a first with sign=+1 and a second with sign=−1. Accordingly, the function may be given by:

$$LLR_{perFeature}[n;\text{sign}]=\text{interp1}(\text{points}[n], \text{sign}\cdot\text{feature}[n])$$

Both the feature generation (LineSegmentBreathingFeaturesSequential) and the breath LLR computation (LineSegmentFeaturesToMetrics) require a knowledge of the sign, and since this knowledge does not exist, they can be made resilient to sign by taking best-case "min/max/abs" over relevant parameters (i.e. choose the option that gives better LLR). This "uncoded" decision increases the LLR and reduces the difference from the null hypothesis—e.g. in case of noise it was found out to add almost +1 to the LLR.

Accordingly, the step of correcting the sign features may depend upon whether the sign decision feedback has determined the sign.

Where the sign is known, then the input of the LLR_per_feature[n,sign] is selected according to the known sign.

Where no such sign has been determined, the sign LLR-s per sign hypothesis may be summed, and the maximum sum out of the two cases may be selected.

The step of summing the corrected LLR values, may generate a breath LLR by summing the LLR_per_feature for all features after the sign features have been selected with the right polarity, and further adding a possible offset:

$$BreathLLR = \sum_{n} LLR_{perFeature}[n;\text{sign}] + LLR\_offset$$

The sign LLR=log(Pr(Sign=1)/Pr(Sign=−1)) may be given by the difference between the LLR obtained for each hypothesis separately:

$$SignLLR = \sum_{n \in SignFeatures} (LLR_{perFeature}[n;+] - LLR_{perFeature}[n;-])$$

It is noted that smoothing of the sign LLR may be performed outside the "LineSegmentGenerateMetrics" module, however the integrated sign decision is useful in order to improve the breathing detection LLR by feeding it with the correct sign. The equation is presented below:

SignLLRAccum[n]=limiter(SignLLRAccum[n−1]+
   SignLLR[n],[−K,K])

It is further noted that although a specific model is presented above, those skilled in the art may prefer alternative models by which the LSM may be generated. Indeed metrics for other features may be determined as required. Moreover in addition or in parallel to the breathing signal analysis, LSMs may be generated for other signals such as heart rate signals as required.

Where appropriate, the line segment model may be used to separate a signal including heartbeat and breathing into the two components. For example where a signal s[n] includes two components s[n]=b[n]+h[n], where b is breathing and h is heartbeat, then b[n] may be estimated by LSM as described herein and h[n] may be determined by the difference of s[n] and b[n].

Technical Notes

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The scope of the disclosed subject matter is defined by the appended claims and includes both combinations and sub combinations of the various features described hereinabove as well as variations and modifications thereof, which would occur to persons skilled in the art upon reading the foregoing description.

The invention claimed is:

1. A method for monitoring life signs in a subject within a target region, the method comprising:
   providing a radar unit comprising:
      at least one transmitter antenna connected to an oscillator and configured to transmit electromagnetic waves into the target region, and
      at least one receiver antenna configured to receive electromagnetic waves reflected by objects within the target region and operable to generate raw data;
   providing a processor unit configured to receive raw data from the radar unit and operable to identify oscillating signals therein;
   the radar transmitting and receiving scanning radiation over the target region;
   the radar generating series of frames, each frame comprising an array of complex values representing radiation reflected from each voxel of the target region during a given time segment;
   the processor collating a series of complex values for each voxel representing reflected radiation for the associated voxel in multiple frames;
   for each voxel determining a center point in the complex plane;
   determining a phase value for each voxel in each frame;
   generating a smooth waveform representing phase changes over time for each voxel;
   selecting a subset of voxels indicative of an oscillating signal; and
   extracting life signs parameters from the oscillating signal, and
wherein the step of selecting a subset of voxels indicative of an oscillating signal comprises:
   generating a line segment model for the oscillating signal;
   extracting characteristic features from the line segment model; and
   executing a verification function to determine if the line segment model indicates a true-breathing signal.

2. The method of claim 1 wherein the step of generating a line segment model comprises:
   selecting bounding points for each significant sloped section in the oscillating signal;
   wherein the bounding points of each significant sloped section comprise:
   a slope start point indicating a significant change from the previous extreme; and
   a slope end point which shares a y-coordinate with the subsequent slope start point of the next significant sloped section.

3. The method of claim 2 wherein the step of generating a line segment model further comprises:
   constructing a trapezoid line segment model by:
   constructing line segments between the bounding points of each significant sloped section;
   constructing line segments between the end point of each significant sloped section and the start point of the next significant sloped section.

4. The method of claim 2 wherein the step of selecting bounding points comprises:
   defining a detection threshold;
   sampling signal values in the oscillating signal until an extreme signal is detected;
   detecting the extreme signal point;
   sampling signal values in the oscillating signal after the extreme signal is detected;
   calculating the difference between each sampled signal and the extreme signal;

if the difference is greater than the detection threshold then:
  setting a slope start point for a line segment following the extreme signal; and
  setting a slope end point for a line segment preceding the extreme signal.

5. The method of claim 4 wherein the step of setting a slope start point for a line segment following the extreme signal comprises selecting the first signal following the extreme signal.

6. The method of claim 4 wherein the step of setting a slope end point for a line segment preceding the extreme signal comprises selecting a signal sample before the extreme having a signal value equal to that of the slope start value.

7. A method for monitoring life signs in a subject within a target region, the method comprising:
  providing a radar unit comprising:
    at least one transmitter antenna connected to an oscillator and configured to transmit electromagnetic waves into the target region, and
    at least one receiver antenna configured to receive electromagnetic waves reflected by objects within the target region and operable to generate raw data;
  providing a processor unit configured to receive raw data from the radar unit and operable to identify oscillating signals therein;
  the radar transmitting and receiving scanning radiation over the target region;
  the radar generating series of frames, each frame comprising an array of complex values representing radiation reflected from each voxel of the target region during a given time segment;
  the processor collating a series of complex values for each voxel representing reflected radiation for the associated voxel in multiple frames;
  for each voxel determining a center point in the complex plane;
  determining a phase value for each voxel in each frame;
  generating a smooth waveform representing phase changes over time for each voxel;
  selecting a subset of voxels indicative of an oscillating signal; and
  extracting life signs parameters from the oscillating signal, and
wherein the step of generating a smooth waveform representing phase changes over time for each voxel comprises rounding each phase value.

8. A system for monitoring life signs in a subject within a target region, the system comprising:
  a radar unit comprising:
    at least one transmitter antenna connected to an oscillator and configured to transmit electromagnetic waves into the target region, and
    at least one receiver antenna configured to receive electromagnetic waves reflected by objects within the target region and operable to generate raw data; and
  a processor unit configured to receive raw data from the radar unit and operable to identify oscillating signals therein;
wherein the processor unit comprises:
  a frame collator comprising a memory unit configured to store a series of complex frame values for each voxel within the target region;
  a voxel segmentation module comprising a processor configured to generate a smooth waveform representing phase changes over time for each voxel;
  a breathing parameter determination module; and
  a heart rate parameter determination module
wherein the heart rate monitor comprises:
  a radar unit directed at a target region
  a foot rest positioned such that the upper side of a foot of a subject placed thereupon is in situated within the target region.

* * * * *